US010837956B2

(12) United States Patent
Haick et al.

(10) Patent No.: US 10,837,956 B2
(45) Date of Patent: *Nov. 17, 2020

(54) SENSOR TECHNOLOGY FOR DIAGNOSING TUBERCULOSIS

(71) Applicant: TECHNION RESEARCH & DEVELOPMENT FOUNDATION LTD., Haifa (IL)

(72) Inventors: Hossam Haick, Haifa (IL); Morad Nakhleh, Haifa (IL)

(73) Assignee: Technion Research & Development Foundation LTD, Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/172,118

(22) Filed: Oct. 26, 2018

(65) Prior Publication Data

US 2019/0064143 A1  Feb. 28, 2019

Related U.S. Application Data

(63) Continuation of application No. 14/438,807, filed as application No. PCT/IL2013/050874 on Oct. 27, 2013, now Pat. No. 10,168,315.

(Continued)

(51) Int. Cl.
*G01N 27/04* (2006.01)
*G01N 33/497* (2006.01)
(Continued)

(52) U.S. Cl.
CPC ........... *G01N 33/497* (2013.01); *A61B 5/082* (2013.01); *G01N 27/04* (2013.01); *G01N 27/127* (2013.01);
(Continued)

(58) Field of Classification Search
CPC .... G01N 27/04; G01N 27/041; G01N 27/045; G01N 2027/222; G01N 33/497; A61B 5/082
See application file for complete search history.

(56) References Cited

U.S. PATENT DOCUMENTS 6,773,926 B1  8/2004 Freund et al.
8,366,630 B2  2/2013 Haick
(Continued)

FOREIGN PATENT DOCUMENTS

CN  102326078  1/2012
WO  1999/27357  6/1999
(Continued)

OTHER PUBLICATIONS

Abaffy et al., (2010) Differential volatile signatures from skin, naevi and melanoma: a novel approach to detect a pathological process. PLoS One 5(11): e13813; 12 pages.
(Continued)

*Primary Examiner* — Alexander S Noguerola
(74) *Attorney, Agent, or Firm* — McDonnell Boehnen Hulbert & Berghoff LLP

(57) ABSTRACT

A sensor technology comprising a single nano-material (gold nanoparticles and/or carbon nanotube) based sensor or a plurality of sensors in conjunction with a pattern recognition algorithm for non-invasive and accurate diagnosis of tuberculosis caused by *M. tuberculosis* bacteria in a subject. The sensor technology is suitable for population screening of tuberculosis, particularly in resource-poor and developing countries.

11 Claims, 17 Drawing Sheets

Related U.S. Application Data

(60) Provisional application No. 61/719,559, filed on Oct. 29, 2012.

(51) Int. Cl.
  G01N 27/22 (2006.01)
  A61B 5/08 (2006.01)
  G01N 27/12 (2006.01)
  G01N 27/26 (2006.01)

(52) U.S. Cl.
  CPC ............. G01N 27/22 (2013.01); G01N 27/26 (2013.01); *G01N 2027/222* (2013.01); *G01N 2033/4975* (2013.01); *G01N 2333/35* (2013.01); *G01N 2800/12* (2013.01); *G01N 2800/26* (2013.01)

(56) References Cited

U.S. PATENT DOCUMENTS

| | | | |
|---|---|---|---|
| 8,481,324 | B2 | 7/2013 | Haick |
| 10,168,315 | B2 * | 1/2019 | Haick ................ A61B 5/082 |
| 2003/0159927 | A1 | 8/2003 | Lewis et al. |
| 2004/0006257 | A1 | 1/2004 | Burch et al. |
| 2004/0127808 | A1 | 7/2004 | Vaughan |
| 2007/0062255 | A1 | 3/2007 | Talton |
| 2009/0239252 | A1 | 9/2009 | Trevejo |
| 2010/0137733 | A1 | 6/2010 | Wang et al. |
| 2010/0291617 | A1 | 11/2010 | Trevejo |
| 2011/0098591 | A1 | 4/2011 | Haick et al. |
| 2011/0269632 | A1 | 11/2011 | Haick |
| 2012/0245434 | A1 | 9/2012 | Haick |
| 2012/0245854 | A1 | 9/2012 | Haick |
| 2013/0034910 | A1 | 2/2013 | Haick |
| 2013/0059758 | A1 | 3/2013 | Haick |
| 2013/0143247 | A1 | 6/2013 | Haick |
| 2013/0150261 | A1 | 6/2013 | Haick |

FOREIGN PATENT DOCUMENTS

| | | |
|---|---|---|
| WO | 2009/066293 | 5/2009 |
| WO | 2010/079490 | 7/2010 |
| WO | 2010/079491 | 7/2010 |
| WO | 2011/148371 | 12/2011 |

OTHER PUBLICATIONS

Amann et al., (2007) Breath analysis: the approach towards clinical applications. Mini Rev Med Chem 7(2): 115-29.

Amann et al., (2010) Analysis of exhaled breath for screening of lung cancer patients. memo—Magazine of European Medical Oncology 3(3): 106-112.

Amann et al., (2010) Chapter 7: Methodological Issues of Sample Collection and Analysis of Exhaled Breath. In: European Respiratory Monograph; Clinical Handbooks for the Respiratory Professional. Edited by Horvath I and de Jongste JC. Published by European Respiratory Society, Latimer Trend & Co. Ltd, Plymouth, UK 49: 96-114.

Barash et al., (2009) Sniffing the Unique "Odor Print" of Non-Small-Cell Lung Cancer with Gold Nanoparticles. Small 5(22): 2618-2624.

Barash et al., (2012) Classification of lung cancer histology by gold nanoparticle sensors. Nanomedicine: Nanotechnology, Biology and Medicine 8(5): 580-589.

Barbieri et al., (2005) Determination of microbial volatile organic compounds from *Staphylococcus pasteuri* against Tuber borchii using solid-phase microextraction and gas chromatography/ion trap mass spectrometry. Rapid Commun Mass Spectrom 19(22): 3411-5.

Brust and Kiely (2002) Some recent advances in nanostructure preparation from gold and silver particles: a short topical review. Colloids and Surfaces A: Physicochemical and Engineering Aspects 202(2-3): 175-186.

Brust et al., (1994) Synthesis of thiol-derivatised gold nanoparticles in a two-phase Liquid-Liquid system. J Chem Soc Chem Commun 7: 801-802 (1994).

Buszewski et al., (2007) Human exhaled air analytics: biomarkers of diseases. Biomedical Chromatography 21(6): 553-566.

Chambers et al., (2011) Novel diagnostics: progress toward a breath test for invasive Aspergillus fumigatus. Med Mycol 49 Suppl 1: S54-61.

Coelho et al., (2007) Breath air analysis and its use as a biomarker in biological monitoring of occupational and environmental exposure to chemical agents. Journal of Chromatography B 853(1-2): 1-9.

Dovgolevsky et al., (2008) Direct observation of the transition point between quasi-spherical and cubic nanoparticles in a two-step seed-mediated growth method. Small 4(11): 2059-66.

Dovgolevsky et al., (2009) Chemically sensitive resistors based on monolayer-capped cubic nanoparticles: towards configurable nanoporous sensors. Small 5(10): 1158-61.

Dovgolevsky et al., (2010) Monolayer-Capped Cubic Platinum Nanoparticles for Sensing Nonpolar Analytes in Highly Humid Atmospheres. J Phys Chem C 14(33): 14042-14049.

Dummer et al., (2011) Analysis of biogenic volatile organic compounds in human health and disease. TrAC Trends in Analytical Chemistry 30(7): 960-967.

Gallagher et al., (2008) Analyses of volatile organic compounds from human skin. Br J Dermatol 159(4): 780-91.

Hakim et al., (2012) Volatile Organic Compounds of Lung Cancer and Possible Biochemical Pathways. Chem Rev 112(11): 5949-5966.

Hostetler et al., (1998) Alkanethiolate Gold Cluster Molecules with Core Diameters from 1.5 to 5.2 nm: Core and Monolayer Properties as a Function of Core Size. Langmuir 14(1): 17-30.

Ibañez and Zamborini (2012) Chemiresistive Sensing with Chemically-Modified Metal and Alloy Nanoparticles. Small 8(2):174-202.

Kneepkens et al., (1994) The potential of the hydrocarbon breath test as a measure of lipid peroxidation. Free Radic Biol Med 17(2): 127-60 and Erratum.

Konvalina and Haick (2012) Effect of Humidity on Nanoparticle-Based Chemiresistors: A Comparison between Synthetic and Real-World Samples. ACS Appl Mater Interfaces 4(1): 317-325.

Lalvani and Pareek (2010) A 100 year update on diagnosis of tuberculosis infection. Br Med Bull 93: 69-84.

Lechner and Rieder (2007) Mass spectrometric profiling of low-molecular-weight volatile compounds—diagnostic potential and latest applications. Curr Med Chem 14(9): 987-95.

Miekisch et al., (2004) Diagnostic potential of breath analysis—focus on volatile organic compounds. Clin Chim Acta 347(1-2): 25-39.

Nakhleh et al., (2014) Detecting active pulmonary tuberculosis with a breath test using nanomaterial-based sensors. Eur Respir J 43(5): 1522-1525.

Naraghi et al., (2010) Use of volatile fingerprints for rapid screening of antifungal agents for efficacy against dermatophyte Trichophyton species. Sensors and Actuators B: Chemical 146(2): 521-526.

Ouyang and Pawliszyn (2006) SPME in environmental analysis. Analytical and Bioanalytical Chemistry 3864): 1059-1073.

Peng et al., (2008) Detecting simulated patterns of lung cancer biomarkers by random network of single-walled carbon nanotubes coated with nonpolymeric organic materials. Nano Lett 8(11): 3631-5.

Peng et al., (2012) Detection of lung, breast, colorectal, and prostate cancers from exhaled breath using a single array of nanosensors. Br J Cancer 103(4): 542-51.

Pennazza et al., (2011) Monitoring of melanoma released volatile compounds by a gas sensors array: From in vitro to in vivo experiments. Sensors and Actuators B: Chemical 154(2): 288-294.

Phillips et al., (2007) Volatile biomarkers of pulmonary tuberculosis in the breath. Tuberculosis (Edinb) 87(1): 44-52.

Phillips et al., (2010) Breath biomarkers of active pulmonary tuberculosis. Tuberculosis (Edinb) 90(2): 145-51.

Phillips et al., (2012) Point-of-care breath test for biomarkers of active pulmonary tuberculosis. Tuberculosis (Edinb) 92(4): 314-20.

(56) References Cited

OTHER PUBLICATIONS

Röck et al., (2008) Electronic nose: current status and future trends. Chem Rev 108(2): 705-25.

Sahgal et al., (2006) *Trichophyton* species: use of volatile fingerprints for rapid identification and discrimination. Br J Dermatol 155(6): 1209-16.

Segev-Bar et al., (2012) Effect of perforation on the sensing properties of monolayer-capped metallic nanoparticle films. J Phys Chem C 116(29: 15361-15368.

Shao et al., (2011) Recent patents on nanosensor for tumor biomarker detection. Nano Biomedicine & Engineering 3(1): 66-72.

Syhre et al., (2009) The scent of *Mycobacterium tuberculosis*—part II breath. Tuberculosis (Edinb) 89(4): 263-6.

Tisch and Haick (2010) Arrays of chemisensitive monolayer-capped metallic nanoparticles for diagnostic breath testing. Reviews in Chemical Engineering 26(5-6): 171-179.

Tisch and Haick (2010) Chapter 4: Sensors Based on Monolayer-Capped Metallic Nanoparticles. In: Chemical Sensors—Fundamentals of Sensing Materials; vol. 2: Nanostructured Materials. Edited by Korotcenkov G. Momentum Press, LLC, New York, USA, pp. 141-202.

Tisch and Haick (2010) Nanomaterials for cross-reactive sensor arrays. MRS Bull 35(10): 797-803.

Turner (2011) Potential of breath and skin analysis for monitoring blood glucose concentration in diabetes. Expert Rev Mol Diagn 11(5): 497-503.

Zhao et al., (1997) Soft lithographic methods for nano-fabrication. J Mater Chem 7(7) 1069-1074.

Zhu et al., (2010) Fast detection of volatile organic compounds from bacterial cultures by secondary electrospray ionization-mass spectrometry. J Clin Microbiol 48(12): 4426-31.

Zilberman et al., (2009) Spongelike structures of hexa-peri-hexabenzocoronene derivatives enhance the sensitivity of chemiresistive carbon nanotubes to nonpolar volatile organic compounds of cancer. Langmuir 25(9): 5411-6.

Zilberman et al., (2010) Carbon nanotube/hexa-peri-hexabenzocoronene bilayers for discrimination between nonpolar volatile organic compounds of cancer and humid atmospheres. Adv Mater 22(38): 4317-20.

Zilberman et al., (2011) Nanoarray of Polycyclic Aromatic Hydrocarbons and Carbon Nanotubes for Accurate and Predictive Detection in Real-World Environmental Humidity. ACS Nano 5(8): 6743-6753.

International Search Report for PCT/IL2013/050874, dated Feb. 11, 2014.

Banday K. M. et al."Use of Urine Volatile Organic Compounds to Discriminate Tuberculosis Patients from Healthy Subjects" Analytical Chemistry, vol. 83 No. 14, pp. 5526-5534, Mar. 2011.

Peng G. et al."Diagnosing lung cancer in exhaled breath using gold nanoparticles" Nature Nanotechnology, vol. 4, pp. 669-673, Aug. 2009.

Fend et al."Prospects for Clinical Application of Electronic-Nose Technology to Early Detection of *Mycobacterium tuberculosis* in Culture and Sputum" J. Clin. Microbiol. vol. 44. No. 6, pp. 2039-2045, Jun 2006.

Peled N. et al."Detection of volatile organic compounds in cattle naturally infected with *Mycobacterium bovis*" Sensors and Actuators B: Chemical , vol. 171-172 , pp. 588-594, May 2012.

Ionsecu R. et al."Detection of Multiple Sclerosis from Exhaled Breath Using Bilayers of Polycyclic Aromatic Hydrocarbons and Single-Wall Carbon Nanotubes" ACS Chem. Neurosci., vol. 2, No. 12, pp. 687-693, Sep. 2011.

Joseph et al., "Gold Nanoparticle/Organic Networks as Chemiresistor Coatings: The Effect of Film Morphology on Vapor Sensitivity," J. Phys. Chem. C 2008, 112, 12507-12514.

Stetter et al., "New sensor arrays and sampling systems for a modular electronic nose," Sensors and Actuators B 69 (2000), pp. 410-419.

Schuster et al., "Classification of breast cancer precursors through exhaled breath," Breast Cancer Research and Treatment, col. 126, No. 3, Dec. 2010, pp. 791-796.

Mgode et al., (2012) *Mycobacterium tuberculosis* volatiles for diagnosis of tuberculosis by Cricetomys rats. Tuberculosis (Edinb) 92(6): 535-542.

Nawrath et al., (2012) The volatiles of pathogenic and nonpathogenic mycobacteria and related bacteria. Beilstein J Org Chem 8: 290-299.

Syhre and Chambers (2008) The scent of *Mycobacterium tuberculosis*. Tuberculosis (Edinb) 88(4): 317-323.

\* cited by examiner

SENSOR TECHNOLOGY FOR DIAGNOSING TUBERCULOSIS

CROSS-REFERENCE TO RELATED APPLICATION

This application is a Continuation of U.S. patent application Ser. No. 14/438,807, filed on Apr. 27, 2015, which is a U.S. national phase of International Application No. PCT/IL2013/050874, filed on Oct. 27, 2013, which claims priority to U.S. Provisional Application No. 61/719,559, filed Oct. 29, 2012, all of which are incorporated by reference herein in their entirety.

FIELD OF THE INVENTION

The present invention relates to sensor technology for diagnosing tuberculosis caused by *M. tuberculosis* bacteria.

BACKGROUND OF THE INVENTION

Tuberculosis (TB) is a common infectious disease caused by mycobacterium, mainly *M. tuberculosis*. It usually attacks the lungs (as pulmonary TB) but can also affect the central nervous system, the lymphatic system, the circulatory system, the genitourinary system, the gastrointestinal system, bones, joints, and even the skin. TB is easily spread by airborne transmission of small droplets. Over 90% of the annual new TB cases and deaths occur in resource-poor and developing countries.

Sputum smear microscopy is the standard diagnostic method used for diagnosing TB. This method is more than 100 years old and fails to detect more than half of all active cases (Lalvani et al., Br. Med. Bull. 93, 69-84 (2010)). The interpretation of the tuberculin skin test relies on individual epidemiological risk factors of infection. This test therefore tends to be inaccurate under certain biological conditions and is incapable of distinguishing between latent TB and active TB infection. Additionally, it is labor-intensive for the patient as well as the health-care provider. Another diagnostic test for TB includes acid-fast bacilli staining of sputum sample. However, this test does not distinguish *M. tuberculosis* from non-tuberculosis mycobacteria and it requires an additional positive smear culture after 8 weeks for definitive diagnosis of pulmonary TB.

In industrialized countries, where TB burden is relatively low, TB diagnosis relies on molecular assays and mycobacterial cultures. In these countries, early positive results can be obtained using assays that determine the production of carbon dioxide or the consumption of oxygen by microorganisms in culture. However, approximately 20 days are required to obtain an accurate positive result.

Nucleic acid amplification tests (NAATs) that identify *M. tuberculosis* in respiratory system within 2-7 hours and interferon γ release assay are two of the more recently developed methods for TB diagnosis. These methods are considered to be more rapid, accurate and sensitive. However, the equipment used in these methods is expensive and it requires technical expertise and/or the testing requires the use of radioactive materials and their disposals. Hence, the current diagnostic techniques are either inaccurate and time consuming, or are expensive and demand highly sophisticated laboratories which are not available in resource-poor and developing countries.

Because of their potential role in the diagnosis of pulmonary diseases, exhaled Volatile Organic Compounds (VOCs) have captured an increased interest in recent years. Chemical analysis, including specific identification and quantification of VOCs in breath samples, has revealed key differences between breath compositions of patients afflicted with several pulmonary diseases as compared to control samples. These pulmonary diseases include asthma, chronic obstructive pulmonary disease, cystic fibroses and lung cancer (WO 2010/079491; U.S. 2013/143247; and U.S. 2013/150261).

The diagnosis of infectious diseases by detecting VOCs that are emitted from infected cells and/or the surrounding microenvironment has been performed. The diagnosis is based on the following principles of cell biology. The cell membrane of bacteria consists primarily of amphipathic phospholipids, carbohydrates and many integral membrane proteins that are distinct for different cell types. When a disease progresses, the cell undergoes structural changes that often lead to oxidative stress, i.e. a peroxidation of the cell membrane that induces VOCs emission. It has been shown that each type of infectious disease is characterized by a unique composition of VOCs (Dummer et al., Trends Anal. Chem., 30, 960-967 (2011)). These VOCs can be detected from samples of bodily fluids or the headspace of a container containing infected cells and/or tissues or directly from exhaled breath in which disease-related changes are reflected through exchange via the blood or directly via the lung airways (Zhu et al., J. Clic. Microbiol., 48, 4426-4431 (2010); and Naraghi et al., Sens. Actuat. B, 146, 521-526 (2010); Abaffy et al., PLOS ONE, 5 (11), e13813, doi:10.1371/journal.pone.0013813 (2010); Sahgal et al., Br. J. Dermatol., 155, 1209-1216 (2006); Turner, Exp. Rev. Mol. Diag., 11, 497-503 (2011); and Pennazza et al., Sens. Actuat. B, 154, 288-294 (2011)).

Specific alterations in VOC compositions of urine and breath samples of TB positive individuals have been reported (Banday et al., Anal. Chem., 83 (14), 5526-5534 (2011)). Phillips et al. used gas-chromatography linked with mass spectrometry (GC-MS) to identify TB-related VOCs, part of which was found in *M. tuberculosis* cultures (Tuberculosis, 90, 145-151 (2010); and Tuberculosis, 87, 44-52 (2007)). Analyzing these VOCs using pattern recognition algorithms provided the accurate classification of 80-84% of the samples (Phillips et al., Tuberculosis, 92, 314-320 (2012)). Banday et al. showed significant alterations in VOCs concentrations in urine samples collected from TB patients using GC-MS (Anal. Chem., 83, 5526-5534 (2011)).

The use of GC-MS analysis for the detection of VOCs as breath biomarkers for TB has several disadvantages for use in clinical point-of-care applications. In particular, this technique utilizes bulky equipment which is relatively expensive and complicated to operate. In addition, it involves a pre-concentrating step which increases the risk of contamination and/or loss of analytes (Buszewski et al., Biomed. Chromatogr., 21, 553-566 (2007)). Furthermore, the accuracy obtained in these measurements is relatively low and it does not meet the criteria which is required for a TB screening test. Syhre et al. used GC-MS for specific detection of nicotinic acid as an indication for active TB (Tuberculosis, 89, 263-266 (2009)). The method required the in-vitro methylation of the nicotinic acid prior to measurements. Furthermore, this method could not provide reliable results for smoking individuals. Peled et al. identified unique VOCs or a VOC profile in the breath of cattle infected with *M. bovis* (bovine tuberculosis) using GC-MS analysis. The unique profile of VOCs was used to design a nanotechnology-based array of sensors for detection of *M. bovis*-infected cattle via breath (Sens. Actuat. B, 171-172, 588-594 (2012); FIG. 11).

U.S. 2010/0291617 and U.S. 2009/0239252 disclose methods and devices for identifying *M. tuberculosis* bacteria in a sample comprising the detection of one or more volatile organic compounds indicative of a presence of or response to treatment or resistance of the *M. tuberculosis* bacteria in the sample.

U.S. 2010/0137733 discloses a method for detecting whether a subject has tuberculosis or monitoring a tuberculosis subject, said method comprising: contacting breath from said subject with an apparatus, said apparatus having a gas chromatograph, wherein said gas chromatograph is fluidly coupled to a detector array to produce a signal; and analyzing said signal from the detector array to determine whether said subject has tuberculosis.

U.S. 2007/0062255 discloses an apparatus for collecting and detecting compounds in a human breath sample comprising: a handheld sample collector comprising a sorbent phase; a breath analyzer comprising a thermal desorption column; two or more sensors for detection of breath compounds; and a flow controller for controlling the transfer of breath compounds from the sample collector into the breath analyzer, wherein the handheld sample collector and breath analyzer are configured for fluid communication with each other so that breath compounds from the sample collector can pass into the breath analyzer for detection.

U.S. 2004/0127808 discloses a method for assessing a disease in a subject, said method comprising: collecting condensate from a subject's breath, said condensate having an acetic acid or acetate concentration or both an acetic acid and acetate concentration; testing said condensate to determine said acetic acid or acetate concentration or both said acetic acid and acetate concentrations; and evaluating said acetic acid or acetate concentration or both said acetic acid and acetate concentrations to determine the presence, absence or status of a disease in the subject.

At present, no simple and reliable technique is available for TB diagnosis, suitable for population screening. There remains an unmet need for a rapid, accurate, and cost-effective TB diagnostic tool that can be used at resource-poor health facilities, including central reference laboratories, hospital and clinic laboratories, and ultimately at the point-of-care.

SUMMARY OF THE INVENTION

The present invention is directed to a sensor for diagnosing tuberculosis caused by *M. tuberculosis* bacteria in a subject, the sensor comprising at least one of gold nanoparticles coated with dodecanethiol and single walled carbon nanotubes coated with 2-methyl-2-butene. The present invention is further directed to a system comprising a plurality of sensors, a detection means and a pattern recognition analyzer and use thereof for diagnosing tuberculosis caused by *M. tuberculosis* bacteria in a non-invasive manner.

The present invention is based in part on the unexpected finding that a single sensor comprising gold nanoparticles coated with dodecanethiol or a single sensor comprising single walled carbon nanotubes coated with 2-methyl-2-butene provide enhanced sensitivity and selectivity for volatile biomarkers which are indicative of the presence of active tuberculosis caused by *M. tuberculosis* bacteria in a subject. The use of a plurality of sensors in conjunction with a pattern recognition algorithm provides the discrimination between TB positive and control populations with sensitivity, specificity and accuracy of over 90% thus offering significant advantages over the hitherto used diagnostic tests. The sensitivity, specificity and accuracy are not affected by confounding factors including smoking habits, HIV infection, drug consumption and/or combinations thereof. The present invention thus provides a fast and reliable diagnosis of tuberculosis, suitable for population screening.

According to one aspect, the present invention provides a sensor for diagnosing tuberculosis caused by *M. tuberculosis* bacteria in a subject, the sensor comprising gold nanoparticles coated with dodecanethiol. In one embodiment, the sensor consists essentially of gold nanoparticles coated with dodecanethiol. In another embodiment, the gold nanoparticles coated with dodecanethiol are in a configuration selected from 1D wires, 2D films, and 3D assemblies. Each possibility represents a separate embodiment of the present invention. In additional embodiments, the gold nanoparticles have a morphology selected from a cubic, a spherical, and a spheroidal morphology. Each possibility represents a separate embodiment of the present invention. In further embodiments, the gold nanoparticles have diameters ranging from about 3 nanometer to about 5 nanometers.

According to another aspect, the present invention provides a sensor for diagnosing tuberculosis caused by *M. tuberculosis* bacteria in a subject, the sensor comprising single walled carbon nanotubes coated with 2-methyl-2-butene. In one embodiment, the sensor consists essentially of single walled carbon nanotubes coated with 2-methyl-2-butene. In another embodiment, the single walled carbon nanotubes coated with 2-methyl-2-butene are organized in a random network configuration. In additional embodiments, the single walled carbon nanotubes have diameters ranging from about 0.9 nanometer to about 5 nanometers, and lengths ranging from about 1 micrometer to about 50 micrometers.

In some embodiments, the sensor of the present invention further comprises a substrate and a plurality of electrodes on said substrate. In various embodiments, the gold nanoparticles coated with dodecanethiol or the single walled carbon nanotubes coated with 2-methyl-2-butene form a conductive path between the electrodes. In certain embodiments, upon adsorption of at least one VOC indicative of tuberculosis caused by *M. tuberculosis* bacteria on the dodecanethiol or 2-methyl-2-butene coating, the electrical conductivity between the electrodes changes thereby providing a measurable signal indicative of tuberculosis.

In some embodiments, the sensor of the present invention is configured in a form selected from the group consisting of a capacitive sensor, a resistive sensor, a chemiresistive sensor, an impedance sensor, and a field effect transistor sensor. Each possibility represents a separate embodiment of the present invention. In exemplary embodiments, the sensor is configured as a chemiresistor.

In certain embodiments, the sensor further comprises a detection means comprising a device for measuring changes in resistance, conductance, alternating current (AC), frequency, capacitance, impedance, inductance, mobility, electrical potential, optical property or voltage threshold. Each possibility represents a separate embodiment of the present invention.

In particular embodiments, the present invention provides a sensor for diagnosing tuberculosis caused by *M. tuberculosis* bacteria in a subject, the sensor consisting essentially of at least one of gold nanoparticles coated with dodecanethiol and single walled carbon nanotubes coated with 2-methyl-2-butene, a substrate, a plurality of electrodes on said substrate, and a detection means.

In several embodiments, the sensor of the present invention is used in conjunction with either one of a breath concentrator and a dehumidifying unit. Each possibility represents a separate embodiment of the present invention.

In various embodiments, the sensor of the present invention is used in conjunction with either one of a chemiresistor, a chemicapacitor, a quartz crystal microbalance, a bulk acoustic wave (BAW) and a surface acoustic wave (SAW) resonator, an electrochemical cell, a surface plasmon resonance (SPR), and an optical spectroscope. Each possibility represents a separate embodiment of the present invention.

According to another aspect, the present invention provides a method of diagnosing tuberculosis caused by *M. tuberculosis* bacteria in a subject, the method comprising the steps of: (a) providing a sensor comprising gold nanoparticles coated with dodecanethiol; (b) exposing the sensor to a test sample selected from exhaled breath and at least one bodily fluid or secretion of the subject; (c) measuring an electrical signal upon exposure of the sensor to the test sample using a detection means; and (d) diagnosing tuberculosis caused by *M. tuberculosis* bacteria if the electrical signal is greater than a reference.

According to yet another aspect, the present invention provides a method of diagnosing tuberculosis caused by *M. tuberculosis* bacteria in a subject, the method comprising the steps of: (a) providing a sensor comprising single walled carbon nanotubes coated with 2-methyl-2-butene; (b) exposing the sensor to a test sample selected from exhaled breath and at least one bodily fluid or secretion of the subject; (c) measuring an electrical signal upon exposure of the sensor to the test sample using a detection means; and (d) diagnosing tuberculosis caused by *M. tuberculosis* bacteria if the electrical signal is greater than a reference.

In certain embodiments, the electrical signal measured upon exposure of the sensor to the test sample is selected from the group consisting of resistance, conductance, alternating current (AC), frequency, capacitance, impedance, inductance, mobility, electrical potential, and voltage threshold. Each possibility represents a separate embodiment of the present invention.

According to some aspects and embodiments, the present invention provides a system comprising a plurality of sensors, for example between 2 and 6 sensors, selected from the group consisting of gold nanoparticles coated with dodecanethiol, single walled carbon nanotubes coated with 2-methyl-2-butene, and a combination thereof, and further comprising a detection means and a processing unit comprising a learning and pattern recognition analyzer wherein the learning and pattern recognition analyzer receives sensor signal outputs and compares them to stored data. In particular embodiments, the system comprises two sensors wherein each sensor comprises gold nanoparticles coated with dodecanethiol. In further embodiments, the system comprises a plurality of sensors comprising at least one sensor comprising gold nanoparticles coated with dodecanethiol and at least one sensor comprising single walled carbon nanotubes coated with 2-methyl-2-butene.

In other aspects and embodiments, the present invention provides a method of diagnosing tuberculosis caused by *M. tuberculosis* bacteria in a subject, the method comprising the steps of: (a) providing a system comprising a plurality of sensors selected from the group consisting of gold nanoparticles coated with dodecanethiol, single walled carbon nanotubes coated with 2-methyl-2-butene, and a combination thereof, and further comprising a detection means and a processing unit comprising a learning and pattern recognition analyzer wherein the learning and pattern recognition analyzer receives sensor signal outputs and compares them to stored data; (b) exposing the sensors to a test sample selected from exhaled breath and at least one bodily fluid or secretion of the subject; (c) measuring a response induced parameter from the sensors upon exposure to the test sample using a detection means to generate a response pattern; and (d) using a pattern recognition algorithm to analyze the response pattern by comparing it to stored data obtained from a control sample whereby significantly different response pattern of the test sample as compared the control sample is indicative of tuberculosis caused by *M. tuberculosis* bacteria.

In some embodiments, step (c) comprises measuring a plurality of response induced parameters from the sensors upon exposure to the test sample to generate a plurality of response patterns. In one embodiment, the step of measuring a plurality of response induced parameters comprises measuring a plurality of electrical signals from the sensors upon exposure to a test sample. In other embodiments, the step of measuring a plurality of response induced parameters comprises measuring an electrical signal from the sensors upon exposure to a test sample and fitting the electrical signal to a function or a plurality of functions whereby the response induced parameters are selected from function constants, function coefficients, and a combination thereof. Each possibility represents a separate embodiment of the present invention. In yet other embodiments, the step of measuring a plurality of response induced parameters comprises measuring an electrical signal from the sensors upon exposure to a test sample and processing the measured electrical signal followed by the extraction of the plurality of response induced parameters. In particular embodiments, the step of processing the measured electrical signal comprises normalization of the measured electrical signal, calibration of the measured electrical signal or a combination thereof. Each possibility represents a separate embodiment of the present invention.

In certain embodiments, the response induced parameter is selected from the group consisting of steady state normalized response, the time interval for obtaining steady state normalized response, and the time interval for reaching baseline after removal of the test sample. Each possibility represents a separate embodiment of the present invention.

In other embodiments, the response induced parameter is selected from the group consisting of the normalized change of sensor signal at the peak of the exposure, the normalized change of sensor signal at the middle of the exposure, the normalized change of sensor signal at the end of the exposure, and the area under the curve of the sensor signal. Each possibility represents a separate embodiment of the present invention.

In particular embodiments, the response induced parameter is selected from the group consisting of full non steady state response at the beginning of the signal, full non steady state response at the beginning of the signal normalized to baseline, full non steady state response at the middle of the signal, full non steady state response at the middle of the signal normalized to baseline, full steady state response, full steady state response normalized to baseline, area under non steady state response, area under steady state response, the gradient of the response upon exposure to the test sample, the gradient of the response upon removal of the test sample, the time required to reach a certain percentage of the response, such as the time required to reach 10%, 20%, 30%, 40%, 50%, 60%, 70%, 80%, 90% or 100% of the response upon exposure to the test sample, and the time required to reach a certain percentage of the response, such as the time required to reach 100%, 90%, 80%, 70%, 60%, 50%, 40%, 30%, 20% or 10% of the response upon removal of the test sample. Each possibility represents a separate embodiment of the present invention.

According to some aspects and embodiments, the learning and pattern recognition analyzer comprises at least one algorithm selected from the group consisting of artificial neural network algorithms, principal component analysis (PCA), support vector machine (SVM), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor. Each possibility represents a separate embodiment of the present invention. In one embodiment, the at least one algorithm is principal component analysis (PCA).

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

(FIG. 2A) Schematic representation of the gold nanoparticle-based sensors of the present invention. (FIG. 2B) Schematic representation of the carbon nanotube-based sensors of the present invention. (FIG. 2C) Resistance recording of multiple sensors, prior to (left), during (middle), and after (recovery; right) exposure to breath samples.

(FIG. 4B) gold nanoparticles coated with 2-ethylhexanethiol; (FIG. 4C) single walled carbon nanotubes coated with PAH1; (FIG. 4D) single walled carbon nanotubes coated with PAH2; and (FIG. 4E) single walled carbon nanotubes coated with PAH3.

FIGS. 5A, 5B), sensor 2 (S2; FIGS. 5C, 5D) and sensor 3 (S3; FIGS. 5E, 5F). Each circle represents one training sample and each star represents one blind sample where samples from the validation set with responses lower than the threshold were classified as TB positive and are marked as open stars. The dashed lines in FIGS. 5D, 5F and the middle dashed line in FIG. 5B represent Youden's cut-point. The top and bottom lines in FIG. 5B represent rule-in and rule-out cut-points, respectively.

DETAILED DESCRIPTION OF THE INVENTION

Figure 1:
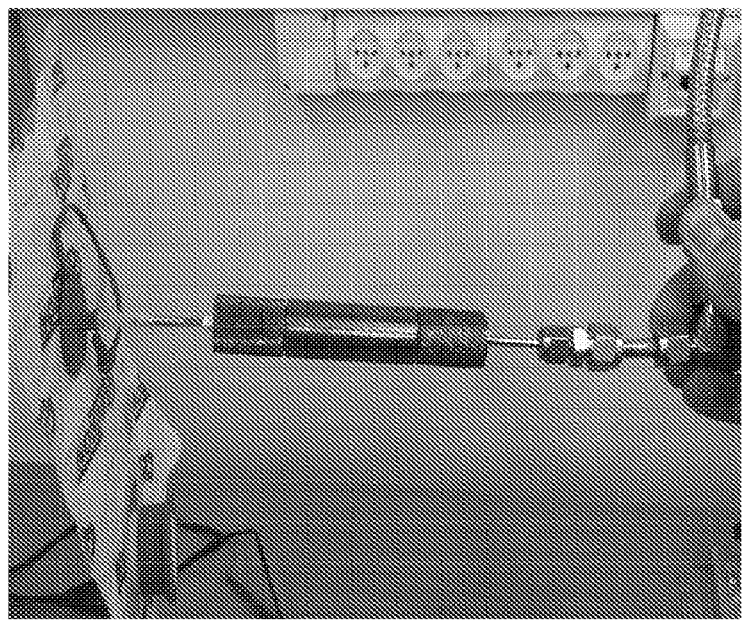
FIG. 1. A photograph of the manual thermal desorption system.

The present invention is directed to the diagnosis of tuberculosis caused by *M. tuberculosis* bacteria using a single sensor comprising gold nanoparticles coated with dodecanethiol or single walled carbon nanotubes coated with 2-methyl-2-butene.

An Artificial Olfactory System (AOS) usually contains an array of chemically modified, cross-reactive nanomaterial-based sensors in conjunction with pattern recognition algorithms. The system can be trained to recognize repeatable compositions which characterize a specific disease to afford its diagnosis. The system provides a different and unique response to a mixture of VOCs indicative of a disease in a subject (Tisch et al., MRS Bull., 35, 797-803 (2012)). AOS systems have already been trained to successfully diagnose various diseases by analyzing individual VOCs in complex multi-component media, for example in human exhaled breath samples (Hakim et al., Chem. Rev., 112 (11), 5949-5966 (2012); Barash et al., Small, 5 (22), 2618-2624 (2009); Barash et al., NanoMed., 8 (5), 580-589 (2012); Peng et al., J. Cancer, 103 (4), 542-551 (2012); Peng et al., Nature Nanotech., 4, 669-673 (2009); Ionescu et al., ACS Chem. Neurosc., DOI: 10.1021/cn2000603 (2011); Peng et al., Br. J. Cancer, 103, 542-551 (2010); Tisch et al., Rev. Chem. Eng., 26, 171-179 (2010); Tisch et al., MRS Bull. 35, 797-803 (2010); WO 2009/066293; WO 2010/079490; WO 2011/148371; U.S. 2012/245854; U.S. 2012/245434; U.S. 2013/034910; U.S. 2013/059758; U.S. Pat. Nos. 8,366,630; and 8,481,324). Recently, it has been reported that AOS systems can be used to detect bovine tuberculosis (Peled et al., Sensors and Actuators B, 171-172, 588-594 (2012)).

The present invention provides for the first time a highly sensitive and specific sensor comprising gold nanoparticles coated with dodecanethiol or single walled carbon nanotubes coated with 2-methyl-2-butene which can be used for the diagnosis of tuberculosis caused by *M. tuberculosis* bacteria in a subject. The sensor of the present invention provides a simple and accurate YES answer when detecting minute amounts (less than 1 ppm) of at least one VOC indicative of tuberculosis caused by *M. tuberculosis* bacteria in breath samples or samples of bodily fluids, without the need for post-measurement analysis. The sensor can thus be used as a non-invasive, portable, and cost-effective diagnostic tool for population screening and early detection of tuberculosis caused by *M. tuberculosis* bacteria. When used in a system comprising an array of sensors in conjunction with a pattern recognition algorithm, an identification of TB positive subjects and their differentiation form TB negative and healthy controls with sensitivity, specificity and accuracy of over 90% could be achieved. The sensing signals of the sensors of the present invention are not affected by confounding factors, including smoking habits, the use of several TB medications, and HIV co-infection of the TB patients. The sensors of the present invention are thus suitable for use as a point-of-care screening tool for early detection of active TB. The sensors do not require sophisticated laboratory equipment or experienced operators, thus being particularly advantages for use in resource-poor and developing countries.

Upon adsorption of a VOC on an organic coating (dodecanethiol or 2-methyl-2-butene) of a conductive or semiconductive material (gold nanoparticles or single walled carbon nanotubes), a change in structural configuration occurs. This change can be translated into an electrical signal which is caused by the formation of a conductive path or plurality of conductive paths between at least two conducting elements (e.g. electrodes). The electrical signal upon VOC exposure is determined by the nature of the interaction between the VOC and the molecular organic coating. Experimental results have shown 16 statistically different VOCs (derivatives of alkenes, dienes, ethers, methylated alkanes, ketones, and alcohols) in culture positive and culture negative TB samples. The sensors of the present invention are designed to be particularly sensitive and selective to at least one VOC indicative of tuberculosis caused by *M. tuberculosis* bacteria.

In some aspects and embodiments, the present invention provides a sensor for diagnosing tuberculosis caused by *M. tuberculosis* bacteria in a subject, the sensor comprising at least one of gold nanoparticles coated with dodecanethiol and single walled carbon nanotubes coated with 2-methyl-2-butene, wherein the sensor is configured to detect the presence of at least one volatile organic compound indicative of tuberculosis caused by *M. tuberculosis* bacteria in a sample thereby affording TB diagnosis.

In certain aspects and embodiments, the sensors of the present invention comprise a plurality of conducting elements which are coupled to each sensor, thereby enabling the measurement of the electrical signals generated by the sensors. The conducting elements may include a source and a drain electrode separated from one another by a source-drain gap. The conducting elements may further comprise a gate electrode wherein the electrical signal may be indicative of the change in structural configuration under the influence of a gate voltage.

The conducing elements may comprise metals such as Au, Ag, Ti/Pd or Pt electrodes and may further be connected by interconnecting wiring. The distance between adjacent electrodes defines the sensing area. Accordingly, different configurations of the electrodes in the sensors of the present invention may be fabricated as is known in the art. Typically, the distance between adjacent electrodes in each sensor ranges between about 0.01-5 mm. In some embodiments, the gold nanoparticles coated with dodecanethiol or the single walled carbon nanotubes coated with 2-methyl-2-butene are casted on a plurality of interdigitated electrodes on a suitable substrate. The substrate, according to the principles of the present invention may be a substantially flexible or substantially rigid substrate. Each possibility represents a separate embodiment of the present invention. In some embodiments, the substantially flexible substrate comprises a polymer selected from the group consisting of polyimide, polyamide, polyimine, polyethylene, polyester, polydimethylsiloxane, polyvinyl chloride, and polystyrene. Each possibility represents a separate embodiment of the present invention. In yet other embodiments, the substantially flexible or rigid substrate comprises silicon dioxide. In other embodiments, the substantially flexible substrate comprises a silicon rubber. In certain embodiments, the substantially rigid substrate is selected from the group consisting of metals, insulators, semiconductors, semimetals, and combinations thereof. Each possibility represents a separate embodiment of the present invention. In one embodiment, the substantially rigid substrate comprises silicon dioxide on a silicon wafer. In another embodiment, the substantially rigid substrate comprises a substantially rigid polymer. In yet another embodiment, the substantially rigid substrate comprises indium tin oxide. Exemplary substrates within the scope of the present invention include, but are not limited to, silicon, glass, ceramic material, PVC 200, Kapton® 50, Kapton® 127, Kapton® b. 131, PET 125, Mylar® 36, Mylar® 50 and the like. Each possibility represents a separate embodiment of the present invention.

The sensor signal can be detected by a detection means. Suitable detection means include devices which are susceptible to a change in any one or more of resistance, conductance, alternating current (AC), frequency, capacitance, impedance, inductance, mobility, electrical potential, optical property and voltage threshold. Each possibility represents a separate embodiment of the present invention. In additional embodiments, the detection means includes devices which are susceptible to a change in any one or more of optical signal (detected by e.g. spectroscopic ellipsometry), florescence, chemiluminescence, photophorescence, bending, surface acoustic wave, piezoelectricity and the like. Each possibility represents a separate embodiment of the present invention.

The sensors of the present invention can be configured as any one of the various types of electronic devices, including, but not limited to, capacitive sensors, resistive sensors, chemiresistive sensors, impedance sensors, field effect transistor sensors, and the like, or combinations thereof. Each possibility represents a separate embodiment of the present invention. In a non-limiting example, the sensors of the present invention are configured as chemiresistive sensors (i.e. chemiresistors).

Sensors can be formed on suitable substrates using a variety of techniques well known in the art. Exemplary techniques include, but are not limited to, (i) Random deposition from solution by drop casting, spin coating, spray coating and the like. Each possibility represents a separate embodiment of the present invention.

(ii) Field-enhanced or molecular-interaction-induced deposition from solution. Each possibility represents a separate embodiment of the present invention.

(iii) Langmuir-Blodgett or Langmuir-Schaefer techniques. Each possibility represents a separate embodiment of the present invention.

(iv) Soft lithographic techniques, such as micro-contact printing (mCP), replica molding, micro-molding in capillaries (MIMIC), and micro-transfer molding (mTM). Each possibility represents a separate embodiment of the present invention.

(v) Various combinations of Langmuir-Blodgett or Langmuir-Schaefer techniques with soft lithographic techniques. Each possibility represents a separate embodiment of the present invention.

(vi) Printing on solid-state or flexible substrates using an inject printer designated for printed electronics.

According to some aspects and embodiments, the sensors of the present invention may be used in conjunction with a breath concentrator and/or a dehumidifying unit.

Breath concentrators that are within the scope of the present invention include, but are not limited to, I. Solid Phase Microextraction (SPME)—The SPME technique is based on a fiber coated with a liquid (polymer), a solid (sorbent), or combination thereof. The fiber coating extracts the compounds from the sample either by absorption (where the coating is liquid) or by adsorption (where the coating is solid). The SPME fiber is then inserted directly into the sensing apparatus for desorption and subsequent analysis (Ouyang, et at, Anal. Bioanal. Chem., 386, 1059-1073 (2006); Coelho et al., J. Chromatography B, 853, 1-9 (2007)).

II. Sorbent Tubes—Sorbent tubes are typically composed of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Chemicals are trapped onto the sorbent material throughout the sampling period. This technique was developed by the U.S. National Institute for Occupational Safety and Health (NIOSH).

III. Cryogenic Condensates—Cryogenic condensation is a process that allows recovery of volatile compounds for reuse. The condensation process requires very low temperatures so that the volatile compounds can be condensed. Traditionally, chlorofluorocarbon (CFC) refrigerants have been used to induce condensation. Currently, liquid nitrogen is used in the cryogenic (less than −160° C.) condensation process.

A dehumidifier that is within the scope of the present invention includes, but is not limited to, I. A device which draws moist air through cold refrigerated coils—using this approach, air moisture condenses into droplets as it passes through cold refrigerated coils into a container. "Dried" air is then brought to its original temperature and returned to the sensing apparatus.

II. Silica Gel—is an amorphous form of silicon dioxide, which is synthetically produced in the form of hard irregular granules or beads. A microporous structure of interlocking cavities provides a very high surface area (800 square meters per gram). This unique structure renders the silica gel as a high capacity desiccant. Water molecules adhere to the surface of the silica gel due to its low vapor pressure as compared to the surrounding air. When pressure equilibrium is reached, the adsorption ceases. Thus, the higher the humidity of the surrounding air, the larger the amount of water that is adsorbed before equilibrium is reached. Silica gel is advantageous as a drying substance since the process of drying does not require any chemical reaction and it does not produce any by products or side effects.

III. Activated carbon—is formed by processing charcoal to an extremely porous carbon substance. Due to its high degree of microporosity, the activated carbon possesses a very large surface area available for chemical reactions. Sufficient activation may be obtained solely from the high surface area, though further chemical treatments often enhance the adsorbing properties of the material.

IV. Desiccant Molecular Sieves—are synthetically produced, highly porous crystalline metal-alumino silicates. They are classified by the many internal cavities of precise diameters, namely, 3 Å, 4 Å, 5 Å, and 10 Å. Adsorption occurs only when molecules to be adsorbed have smaller diameters than the cavity openings. Molecules of high polarity are better adsorbed onto the molecular sieves. Molecular sieves adsorb water molecules and other contaminants from liquids and gases down to very low levels of concentrations, often to 1 ppm.

According to the invention, the sensors may be used in conjunction with either one of a chemiresistor, a chemicapacitor, a quartz crystal microbalance, a bulk acoustic wave (BAW) and a surface acoustic wave (SAW) resonator, an electrochemical cell, a surface plasmon resonance (SPR), and an optical spectroscope. Each possibility represents a separate embodiment of the present invention. In certain embodiments, the sensors of the present invention are not used in conjunction with a gas-chromatography linked with mass spectrometry (GC-MS).

According to one embodiment, the single-walled carbon nanotubes (SWCNTs) coated with 2-methyl-2-butene of the present invention are arranged in a random network configuration. In some embodiments, the network of SWCNTs can be fabricated by a physical manipulation or in a self-assembly process. The term "self-assembly" as used herein refers to a process of the organization of molecules without intervening from an outside source. The self-assembly process occurs in a solution/solvent or directly on a solid-state substrate.

Main approaches for the synthesis of carbon nanotubes in accordance with the present invention include, but are not limited to, laser ablation of carbon, electric arc discharge of graphite rod, and chemical vapor deposition (CVD) of hydrocarbons. Each possibility represents a separate embodiment of the present invention. Among these approaches, CVD coupled with photolithography has been found to be the most versatile in the preparation of various carbon nanotube devices. In a CVD method, a transition metal catalyst is deposited on a substrate (e.g. silicon wafer) in the desired pattern, which may be fashioned using photolithography followed by etching. The substrate having the catalyst deposits is then placed in a furnace in the presence of a vapor-phase mixture of, for example, xylene and ferrocene. Carbon nanotubes typically grow on the catalyst deposits in a direction normal to the substrate surface. Various carbon nanotube materials and devices are now available from commercial sources.

Other CVD methods include, but are not limited to, the preparation of carbon nanotubes on silica ($SiO_2$) and silicon surfaces without using a transition metal catalyst. Accordingly, areas of silica are patterned on a silicon wafer, by photolithography and etching. Carbon nanotubes are then grown on the silica surfaces in a CVD or a plasma-enhanced CVD (PECVD) process. These methods provide the production of carbon nanotube bundles in various shapes.

The term "single walled carbon nanotubes" as used herein refers to a cylindrically shaped thin sheet of carbon atoms having a wall which is essentially composed of a single layer of carbon atoms which are organized in a hexagonal crystalline structure with a graphitic type of bonding. A nanotube is characterized by the length-to-diameter ratio. It is to be understood that the term "nanotubes" as used herein refers to structures in the nanometer as well as micrometer range.

According to various embodiments, the single-walled carbon nanotubes of the present invention have diameters ranging from about 0.6 nanometers (nm) to about 100 nm and lengths ranging from about 50 nm to about 10 millimeters (mm). More preferably, the single-walled carbon nanotubes have diameters ranging from about 0.7 nm to about 50 nm and lengths ranging from about ranging from about 250 nm to about 1 mm. Even more preferably, the single-walled carbon nanotubes have diameters ranging from about 0.8 nm to about 10 nm and lengths ranging from about 0.5 micrometer (μm) to about 100 μm. Most preferably, the single-walled carbon nanotubes of the present invention have diameters ranging from about 0.9 nm to about 5 nm and lengths ranging from about 1 μm to about 50 μm.

Sensors comprising metal nanoparticles coated with dodecanethiol can be synthesized as is known in the art, for example using the two-phase method (Brust et al., J. Chem. Soc. Chem. Commun., 801, 2 (1994)) with some modifications (Hostetler et al., Langmuir, 14, 24 (1998)). Coated gold nanoparticles can be synthesized by transferring $AuCl_4^-$ from aqueous $HAuCl_4.xH_2O$ solution to a toluene solution by the phase-transfer reagent TOAB. After isolating the organic phase, excess thiols are added to the solution. The mole ratio of thiol:$HAuCl_4.xH_2O$ can vary between 1:1 and 10:1, depending on the thiol used. This is performed in order to prepare mono-disperse solution of gold nanoparticles in average size of about 3-5 nm. For dodecanethiol coated gold nanoparticles a thiol:Au mole ratio of 10:1 is used for nanoparticles with an average diameter of 5 nm. After vigorous stirring of the solution, aqueous solution of reducing agent $NaBH_4$ in large excess is added. The reaction is constantly stirred at room temperature for at least 3 hours to produce a dark brown solution of the thiol-coated Au nanoparticles. The resulting solution is further subjected to solvent removal in a rotary evaporator followed by multiple washings using ethanol and toluene. The gold nanoparticles may have any desirable morphology including, but not limited to, a cubic, a spherical, and a spheroidal morphology. Each possibility represents a separate embodiment of the present invention.

The synthesized coated nanoparticles can then be assembled (e.g. by a self-assembly process) to produce a 1D wire, 2D film or 3D assembly of coated nanoparticles. Each possibility represents a separate embodiment of the present invention.

The present invention further provides a method of diagnosing tuberculosis caused by *M. tuberculosis* bacteria in a subject. The method comprises the step of exposing a single sensor of the present invention to a test sample and measuring an electrical signal upon exposure of the sensor to the test sample using a detection means, whereby if the electrical signal is greater than a reference, a YES answer is obtained to afford the diagnosis of tuberculosis caused by *M. tuberculosis* bacteria. The YES/NO answer can be displayed on a display in conjunct to the sensor without further manipulation or processing.

As used herein, the term "reference" refers to a threshold criterion/value to which measured electrical signals are compared in order to obtain an identification of the presence of tuberculosis caused by *M. tuberculosis* bacteria. The reference can be derived in any one of a number of manners. For example, the reference may be based on a collection of data of samples from subjects known to be afflicted with tuberculosis caused by *M. tuberculosis* bacteria or known to be TB negative. According to certain aspects and embodiments, the reference is determined from statistical analysis of studies that compared VOC profiles of subjects with known clinical outcomes and correlated them with the corresponding electrical signals of the sensors of the present invention. Accordingly, the reference may be obtained from data collected from a sample population of subjects, which acts as a pool of data from which normalized expected differences in electrical responses for TB positive and TB negative subjects can be determined. The reference is then generated by selecting the value of electrical signal that is determined as the cut-off for classifying TB positive and TB negative samples. The reference may be varied according to subject parameters such as age, sex, height, weight, race, interventions, or the like.

According to certain aspects and embodiments, the present invention provides a system comprising a plurality of sensors (sensor array) of the present invention. For example, the system may comprise between 2 and 6 sensors. In some embodiments, the system comprises a sensor of single walled carbon nanotubes coated with 2-methyl-2-butene and a sensor of gold nanoparticles coated with dodecanethiol. In other embodiments, the system comprises two sensors of gold nanoparticles coated with dodecanethiol. The system further comprises a detection means as described herein and a processing unit comprising a learning and pattern recognition analyzer which utilizes at least one algorithm.

Algorithms for sample analysis include, but are not limited to, principal component analysis, Fischer linear analysis, neural network algorithms, genetic algorithms, fuzzy logic pattern recognition, and the like. Each possibility represents a separate embodiment of the present invention. Many of the algorithms are neural network based algorithms. A neural network has an input layer, processing layers and an output layer. The information in a neural network is distributed throughout the processing layers. The processing layers are composed of nodes that simulate the neurons by the interconnection to their nodes. When a neural network is combined with a sensor array, the sensor data is propagated through the networks. In this manner, a series of vector matrix multiplications are performed and unknown analytes (VOCs) can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), support vector machine (SVM), Fisher linear discriminant analysis (FLDA), soft independent modeling of class analogy (SIMCA), K-nearest neighbors (KNN), neural networks, genetic algorithms, fuzzy logic, and the like. Each possibility represents a separate embodiment of the present invention. In some embodiments, Fisher linear discriminant analysis (FLDA) and canonical discriminant analysis (CDA) as well as combinations thereof are used to compare the output signature and the available data from the database.

Multidimensional data analysis of the signals collected from all the sensors in the array can be performed using standard principle component analysis (PCA). PCA is an effective method to reduce multidimensional data space to its main components by determining the linear combinations of the sensor values such that the maximum variance between all data points can be obtained in mutually orthogonal dimensions. The first principle component provides the largest variance between sensor values. The second, third, fourth etc. principal components provide decreasing magnitudes of variance between all data points.

In particular, PCA is a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables. PCA compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows in this matrix.

An additional pattern recognition algorithm within the scope of the present invention is support vector machine (SVM). SVM performs classification by constructing an N-dimensional hyperplane that optimally separates the data into two categories. SVM models are closely related to neural networks. Using a kernel function, SVM models are alternative training methods for polynomial, radial basis function and multi-layer perceptron classifiers in which the weights of the network are found by solving a quadratic programming problem with linear constraints, rather than by solving a nonconvex, unconstrained minimization problem as in standard neural network training. Using an SVM model with a sigmoid kernel function is equivalent to a two-layer, perceptron neural network. Using the SVM model, a predictor variable is called an attribute, and a transformed attribute that is used to define the hyperplane is called a feature. The task of choosing the most suitable representation is known as feature selection. A set of features that describes one case (i.e., a row of predictor values) is called a vector. The output of SVM modeling provides the optimal hyperplane that separates clusters of vectors in a manner that affords cases with one category of the target variable on one side of the plane and cases with the other category on the other size of the plane. The vectors near the hyperplane are the support vectors.

After analysis is completed, the resulting information can, for example, be displayed on display, transmitted to a host computer, or stored on a storage device for subsequent retrieval.

The present invention further provides a method for diagnosing tuberculosis caused by M. tuberculosis bacteria comprising exposing the plurality of sensors to a test sample, measuring a response induced parameter from the sensors upon exposure to the test sample using a detection means to generate a response pattern and analyzing the response pattern by comparing it to stored data obtained from a control sample whereby significantly different response pattern of the test sample as compared the control sample is indicative of tuberculosis caused by M. tuberculosis bacteria. According to the principles of the present invention, the analysis is performed using a learning and pattern recognition algorithm.

The term "significantly different" as used herein refers to a statistically significant quantitative difference between the pattern of the test sample and the pattern of a control sample. A statistically significant difference can be determined by any test known to the person skilled in the art. Common tests for statistical significance include, among others, t-test, ANOVA, Kruskal-Wallis, Wilcoxon, Mann-Whitney and odds ratio. Individual samples (of unknown status) can be compared with data from the reference group (negative control), and/or compared with data obtained from a positive control group known to have tuberculosis caused by M. tuberculosis bacteria. A statistically significant elevation or reduction in the particular response parameter being measured between the test and control sample qualifies as significant difference. A set of control samples or response patterns (positive, negative) can be stored as a reference collection of data for multiple analyses. It will be recognized by one of skill in the art that the determination of whether a test subject has active TB caused by M. tuberculosis bacteria is performed when comparing a response pattern to the appropriate control. For example, if the control is a negative control then significantly different response pattern of the test sample as compared the control sample are indicative of TB caused by M. tuberculosis bacteria. Conversely, if the control is a positive control then significantly different response pattern of the test sample as compared the control sample are indicative of lack of active TB caused by M. tuberculosis bacteria.

According to certain aspects and embodiments, a plurality of response induced parameters are measured. In accordance with these embodiments, the plurality of response induced parameters generate a plurality of patterns which are then conveyed to a learning and pattern recognition analyzer which utilizes an algorithm in order to analyze the signal patterns by comparing them to stored data.

In one embodiment, the step of measuring a plurality of response induced parameters comprises measuring a change in any electrical property such as, hut not limited to the resistance, impedance, capacitance, inductance, conductivity, or optical properties of the sensors upon exposure to a test sample using a detection means and extracting a plurality of response induced parameters from said response. A response induced parameter includes, but is not limited to, steady state normalized response, the time interval for obtaining steady state normalized response, the time required to reach baseline after removal of the test sample, the normalized change of sensor signal at the peak of the exposure, the normalized change of sensor signal at the middle of the exposure, the normalized change of sensor signal at the end of the exposure, and the area under the curve of the sensor signal. Each possibility represents a separate embodiment of the present invention. In other embodiments, the response induced parameter includes, but is not limited to, full non steady state response at the beginning of the signal, full non steady state response at the beginning of the signal normalized to baseline, full non steady state response at the middle of the signal, full non steady state response at the middle of the signal normalized to baseline, full steady state response, full steady state response normalized to baseline, area under non steady state response, area under steady state response, the gradient of the response upon exposure to the test sample, the gradient of the response upon removal of the test sample, the time required to reach a certain percentage of the response, such as the time required to reach 10%, 20%, 30%, 40%, 50%, 60%, 70%, 80%, 90% or 100% of the response upon exposure to the test sample, and the time required to reach a certain percentage of the response, such as the time required to reach 100%, 90%, 80%, 70%, 60%, 50%, 40%, 30%, 20% or 10% of the response upon removal of the test sample. Each possibility represents a separate embodiment of the present invention.

In another embodiment, the step of measuring a plurality of response induced parameters comprises measuring a plurality of responses selected from resistance, impedance, capacitance, inductance, conductivity, and optical properties of the sensors upon exposure to a test sample. Each possibility represents a separate embodiment of the present invention.

In yet another embodiment, the step of measuring a plurality of response induced parameters comprises measuring a change in the resistance, impedance, capacitance, inductance, conductivity, or optical properties of the sensors upon exposure to a test sample and fitting the response to a function or a plurality of functions whereby the response induced parameters are selected from function constants, function coefficients, and a combination thereof. Each possibility represents a separate embodiment of the present invention.

In further embodiments, the step of measuring a plurality of response induced parameters comprises measuring a change in the resistance, impedance, capacitance, inductance, conductivity, or optical properties of the sensors upon exposure to a test sample and processing the signal (e.g. by normalization, calibration etc.) followed by the extraction of the plurality of response induced parameters.

Without being bound by any theory or mechanism of action, by measuring a plurality of response induced parameters upon VOC exposure of the sensors, improved sensitivity and specificity of the analysis can be obtained. This obviates the need for additional sensors and improves the discrimination between subjects suffering from TB caused by *M. tuberculosis* and healthy subjects.

The methods of diagnosis of the present invention can be performed even in the presence of confounding factors selected from smoking, HIV infection, consumption of medication and combinations thereof. Each possibility represents a separate embodiment of the present invention.

The test sample, according to the principles of the present invention is selected from a breath sample and a bodily fluid or secretion of a subject. The sensor or system of the present invention can be directly exposed to a breath sample or sample of bodily fluid or secretion. Alternatively the sensor or system of the present invention can be exposed to the headspace of a container wherein breath samples, bodily fluids or secretions have been deposited. The sensor or system of the present invention can be exposed to breath directly exhaled by the subject through a mouthpiece, without a need for pre-concentrating or dehumidifying the sample. Other possibilities include exhaling into an inert bag and then exposing the collected breath to the sensor or system of the present invention. Bodily fluids or secretions within the scope of the present invention include, but are not limited to, scrum, urine, feces, sweat, vaginal discharge, saliva and sperm. Each possibility represents a separate embodiment of the present invention.

Figure 10:
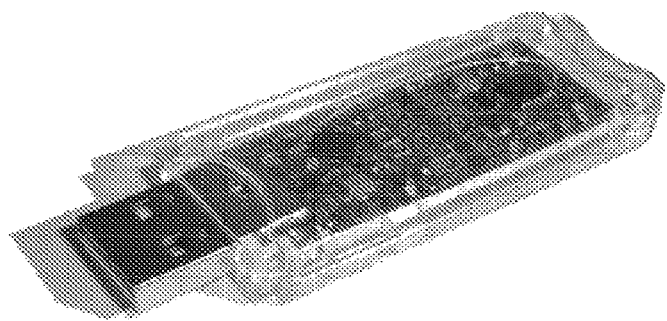
FIG. 10. Illustration of a TB breath testing device according to the present invention with USB port for fast analysis.
Figure 11:
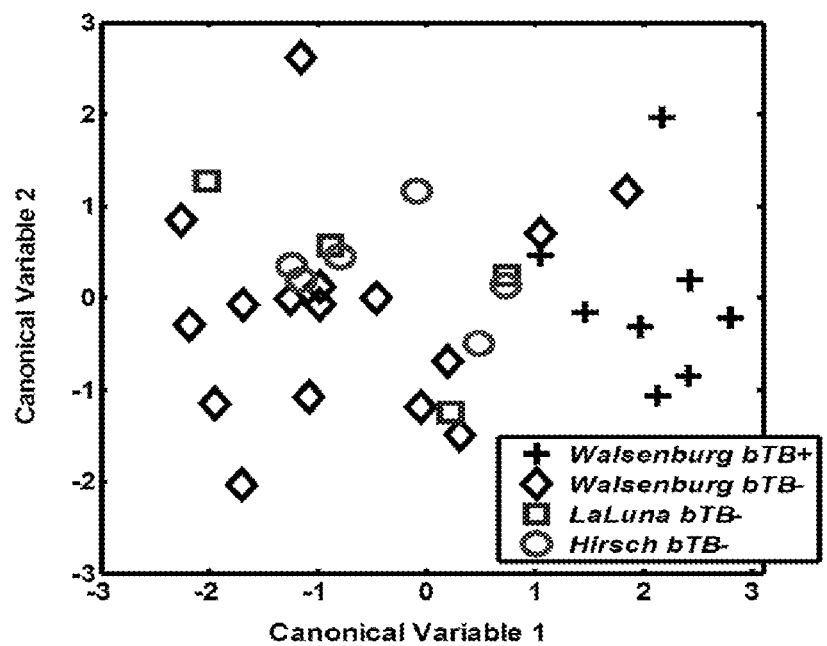
FIG. 11. Discriminant Factor Analysis (DFA) plot showing the classification between bovine TB-infected exemplars (bTB+) and non-infected exemplars (bTB−) based on the response of an array of six nanomaterial-based sensors exposed to animals' breath samples. Each point in the graph belongs to a different exemplar. The bovine TB-infected exemplars belong to a unique dairy from Southern USA, while the non-infected exemplars belong to three different dairies from Southern USA. Bovine tuberculosis was classified with 100% sensitivity and 79% specificity (Peled et al., Sensors and Actuators B, 171-172, 588-594 (2012)).

The present invention provides sensor technology for diagnosing TB caused by *M. tuberculosis* bacteria. The sensor technology of the present invention could be easily adapted as a disposable home- or office-kit for fast TB testing. FIG. 10 illustrates an exemplary device for simple and reliable TB diagnosis in accordance with the present invention. In particular, the devise comprises a sensor according to the present invention mounted on an electronic chip for signal readout and data storage. The device is designed to include an opening at one end adapted to capture the breath of a subject after the removal of a sterile seal. The sensors' readout and software for subsequent data analysis is loaded onto a computer via the USB port at the opposite end of the device. The data could be analyzed within less than a minute, either on-site or via data-link to the doctor's office or to a central server.

As used herein and in the appended claims the singular forms "a", "an," and "the" include plural references unless the content clearly dictates otherwise. Thus, for example, reference to "a pattern recognition algorithm" includes a plurality of such algorithms and equivalents thereof known to those skilled in the art, and so forth.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods
  Study Population
  Subjects who participated in this study were recruited from three sites at Cape-town, South Africa. A total of 210 breath and sputum samples from 210 subjects (18+ years old who had signed an informed consent) were obtained. Twelve samples were damaged during transport and were therefore excluded from the analysis. Study population consisted of two main subgroups as follows: the first group consisted of TB positive group (n=64), which included patients showing at least 2 of the TB classic symptoms, such as coughing for more than 2 weeks, persistent loss of weight for more than 2 weeks and/or a single recorded body temperature>38° C., night sweats, generalized fatigue, hemoptysis and chest pain. The TB positive group also showed positive smear test and/or culture; and the second group (control) consisted of two sub-populations: (1) healthy subjects (n=67) that completed 8 weeks of follow-up without any development of TB symptoms, and (2) TB negative group (n=67), which included subjects that were suspected to have TB infection due to the presentation of classic TB infection symptoms, but showed the combination of all of the following: negative direct sputum smear test, 8 weeks of negative smear culture, and negative Xpert® MTB/RIF test for MTB specific DNA sequences in laboratory examination. Since sputum smear test and culture are known to have relatively low sensitivity, yet very high (close to 100%) specificity, additional methods to verify TB negative subjects were used including 8 weeks of clinical follow-up for subjects that were found to be negative by sputum smear test and culture and nucleic acid amplification tests (NAATs). The main two subgroups were matched in the age of the subjects, male to female ratio, and in the results of previous TB infection tests in their medical history files. The clinical data of the study population is summarized in Table 1.

TABLE 1

Clinical data of the study population

|  | TB positive | Control | P value |
|---|---|---|---|
| Number of Subjects | 64 | 134 |  |
| Mean age ± SD | 35 ± 11 | 38 ± 11 | N.S.§ |
| Positive smear test | 58 (91%) |  |  |
| Positive culture | 43 (67%) |  |  |
| Male | 34 (53%) | 68 (51%) | N.S.§ |
| Past/current smokers | 6/30 (20%) | 55 (41%) | 0.0175 |
| Previous TB | 16 (25%) | 31 (23%) | N.S.§ |
| HIV infected | 25 (39%) | 27 (20%) | 0.008 |
| Mean CD4 ± SD | 247 ± 32 | 250 ± 35 | N.S.§ |
| TB treatment on date of sampling | 52 (81%) | 0 | <0.001 |
| Median days of treatment (range) | 5 (1-14) |  |  |

§Non-significant

Breath Collection, Sample Preparation and Storage

Exhaled alveolar breath was collected in a controlled manner and in the same clinical environment from each subject. The inhaled air was cleared of ambient contaminants by repeatedly inhaling to total lung capacity for 3-5 minutes through a mouthpiece (purchased from Eco Medics, Duerten, Switzerland) that contained a charcoal filter cartridge on the inspiratory port, thus generally reducing over 99.99% of the concentration of exogenous VOCs during inspiration. Unfiltered hospital air was regularly sampled and typical hospital contaminations which were identified in the sampling were disregarded during analysis. Immediately after lung washout, subjects exhaled through a separate exhalation port of the mouthpiece against 10-15 cm $H_2O$ pressure to ensure closure of the vellum so that nasal entrainment of gas was excluded.

Exhaled breath is a mixture of alveolar air and respiratory dead space air. The dead space air was automatically filled into a separate bag, and 750 ml of end tidal expirium was sampled into an inert Mylar bag. It should be emphasized that the described breath collection is a single-step process that does not require exchange between the dead space and alveolar breath bags. Immediately after breath collection, VOCs in the breath samples were trapped and pre-concentrated in two-bed ORBO™ 420 Tenax® TA sorption tubes for gas and vapor sampling (specially treated; 35/60 mesh; 100/50 mg; purchased from Sigma-Aldrich, China) by pumping the content of each collection hag through a sorbent tube (flow rate: 150-200 ml/min). Room air samples were collected by pumping ambient air in the collection room through a sorbent tube for 10 minutes at a rate of 100 ml/min. The sorbent tubes were stored under refrigeration at 4° C., until they were transported in a single shipment and under similar conditions to the laboratory facilities for subsequent breath analysis (Laboratory for Nanomaterial-Based Devices, Technion, Israel). All samples (not including the 12 damaged samples) were analyzed within 6 months from collection.

Breath Sample Analysis

A manual thermal desorption (TD) system was used in order to transfer breath samples from the disposable ORBO™ 420 Tenax® TA sorption tubes into 750 ml inert Mylar bags. The tube was heated to 190° C. for 8 minutes under a constant $N_2$ (99.999% purity) flow of 60 ml/min, using the setup shown in FIG. 1. Breath VOCs were released into the 750 ml Mylar bag. Pulses of breath sample from the Mylar bag were then delivered by a gas sampling system into a stainless steel test chamber containing the nanomaterial-based sensors of the present invention. The test chamber was evacuated (~30 mtorr) between exposures to release VOCs that were adsorbed by the sensors. An Agilent Multifunction switch 34980 was used to measure the resistance of all sensors simultaneously as a function of time. The sensors' baseline responses were recorded for 5 minutes in vacuum, followed by 5 minutes under breath sample exposure, followed by another 5 minutes in vacuum. In order to detect possible malfunctions of the sensors, and to counteract slight drifts of their baseline conditions due to aging and/or poisoning effects, the sensors were daily calibrated by exposing the sensors to known concentrations of three calibration compounds and recording their change in resistance. Specifically, the following calibration procedure was used: the test chamber was evacuated for 5 minutes in order to eliminate possible contaminations, followed by exposure of the sensors to a fixed mixture of three VOCs including 23.8 ppm isopropyl alcohol, 6.3 ppm trimethylbenzene and 1.2 ppm 2-ethylhexanol for a duration of 5 minutes, and then concluded by evacuation of the test chamber for 5 minutes in order to eliminate the calibration compounds from the test chamber.

Figure 2A:
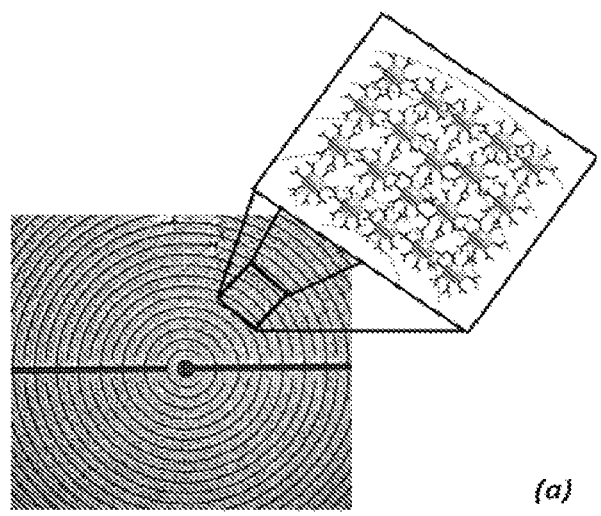
FIGS. 2A-2C.
Figure 2B:
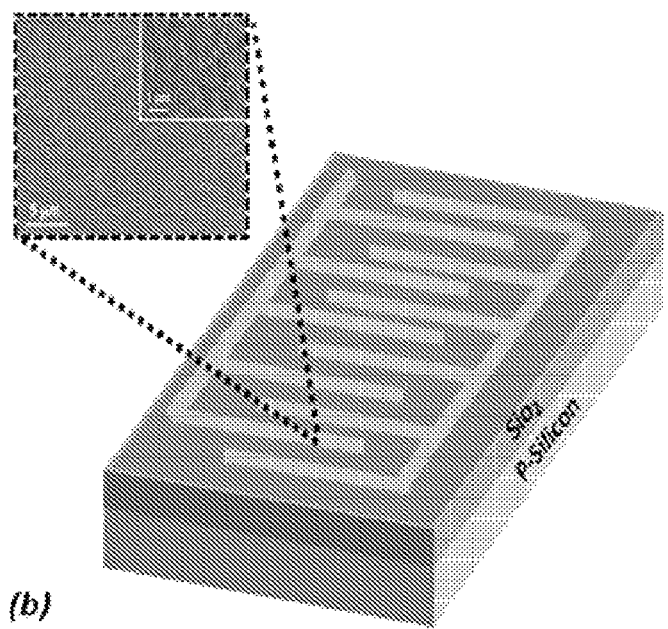
Figure 2C:
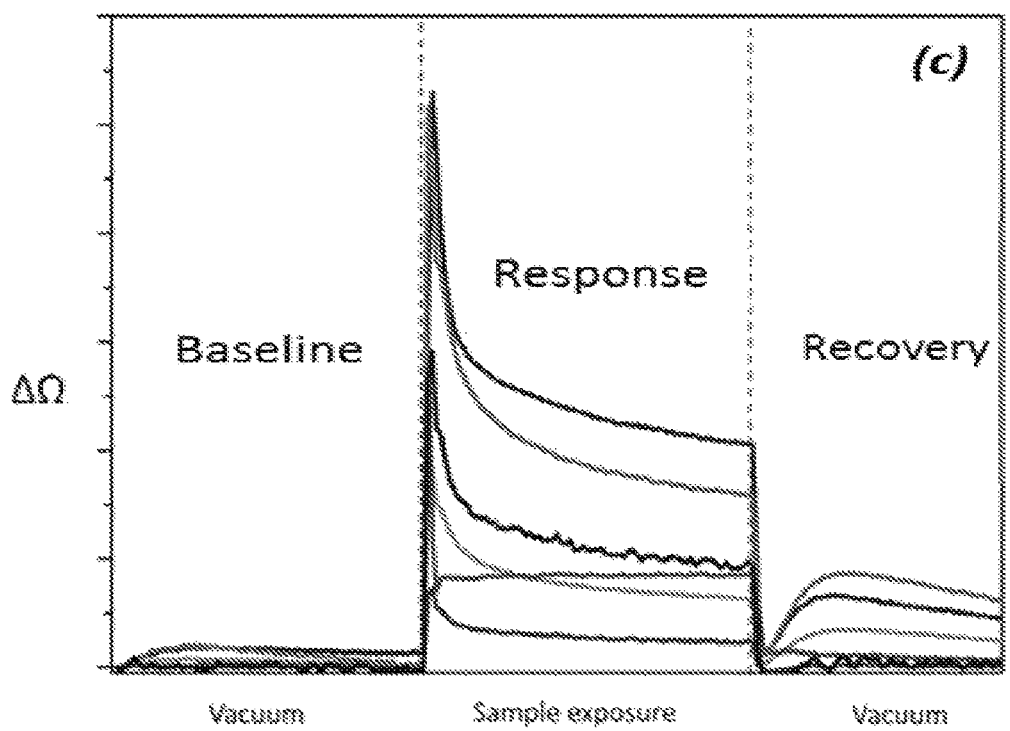

The exposure of the sensors to the breath samples or the calibration compounds resulted in rapid and fully reversible changes of the electrical resistance (FIG. 2C). Four sensing features (response induced parameters) were extracted from the time-dependent resistance response of each sensor: (F1) the normalized change of sensor resistance at the peak of the exposure, (F2) the normalized change of sensor resistance at the middle of the exposure, (F3) the normalized change of sensor resistance at the end of the exposure, and (F4) the area under the curve of the entire measured resistance signal. The net sensing features that were extracted for the breath samples were then divided by the corresponding values that were obtained for the reference calibration compound.

Nanomaterial-Based Sensors and Sensor Fabrication

Twelve nanomaterial-based sensors were used to analyze the breath samples. The sensors were designed as cross-reactive, chemically diverse chemiresistors that were based on two types of nanomaterials: (i) organically coated spherical gold nanoparticles (GNPs, core diameter: 3-4 nm), and (ii) functionalized single walled carbon nanotubes (SW-CNTs). FIG. 2A shows the optical microscopy image of the electrodes circles of organically coated spherical gold nanoparticles of the present invention. The inset shows a schematic representation (not drawn to scale) of films of organically capped spherical gold nanoparticles, which connect the electrodes and form multiple pathways between them. FIG. 2B shows a schematic representation (not drawn to scale) of CNT-based sensors of the present invention. The left inset shows a scanning electron micrograph of SWCNTs which were functionalized with PAH molecules.

Organically capped gold nanoparticles were synthesized as described in Peng et al., Nature Nanotech., 4, 669-673 (2009); Tisch et al., in Chemical Sensors—Nanostructured Materials, Ed. G. Korotcenkov, 2 (2), Ch. 4, 141-202 (2010); Dovgolevsky et al., Small, 4, 2059-2066 (2008); Dovgolevsky et al., Small, 5, 1158-1161 (2009); Dovgolevsky et al., J. Phys. Chem. C, 114, 14042-14049 (2010); WO 2010/079490; and WO 2011/148371, the contents of each of which are hereby incorporated in their entirety; and dispersed in chloroform. Chemiresistive layers were formed by drop-casting the solution onto semi-circular microelectronic transducers, until a resistance of several MΩ was reached. The devices were dried for 2 hours at ambient temperatures and then baked overnight at 50° C. in a vacuum oven. The microelectronic transducers consisted of ten pairs of circular interdigitated (ID) gold electrodes on silicon with 300 nm thermal oxide (Silicon Quest International, Nevada, US). The outer diameter of the circular electrode area was 3 mm, and the gap between two adjacent electrodes and the width of each electrode, was 20 μm each.

Figure 3:
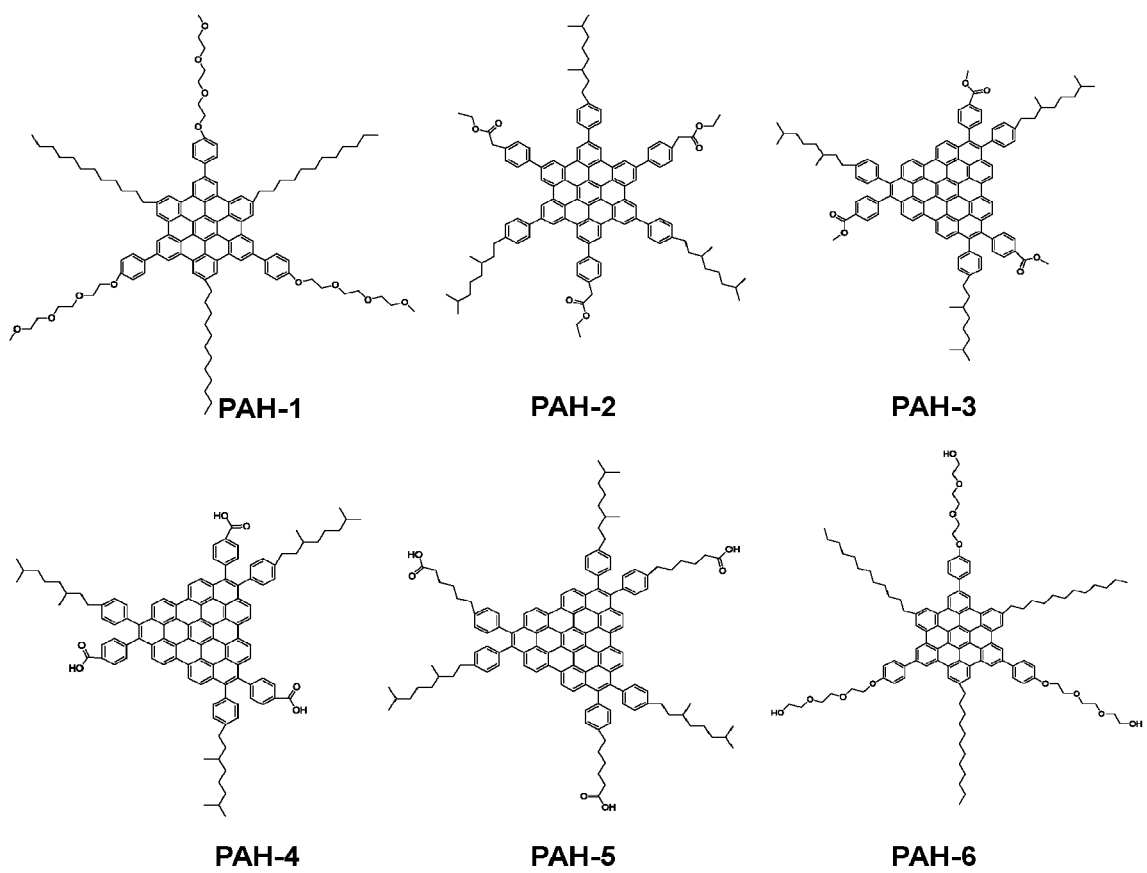
FIG. 3. Structures of PAH derivatives PAH1-PAH6.
Figure 4A:
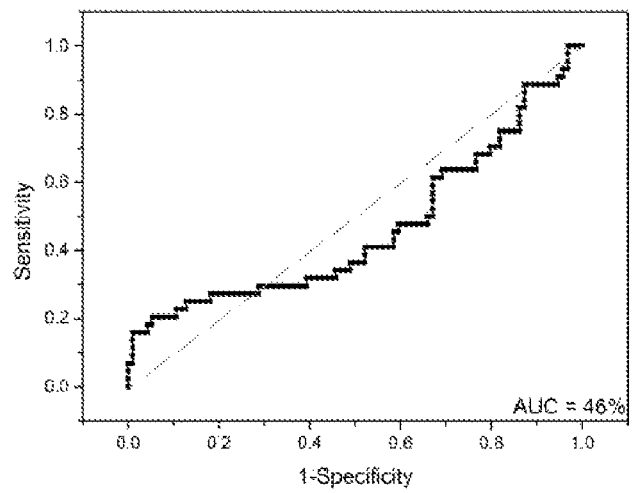
FIGS. 4A-4E. Receiver operating characteristic (ROC) curves of sensors of (FIG. 4A) gold nanoparticles coated with tert-dodecanethiol.
Figure 4B:
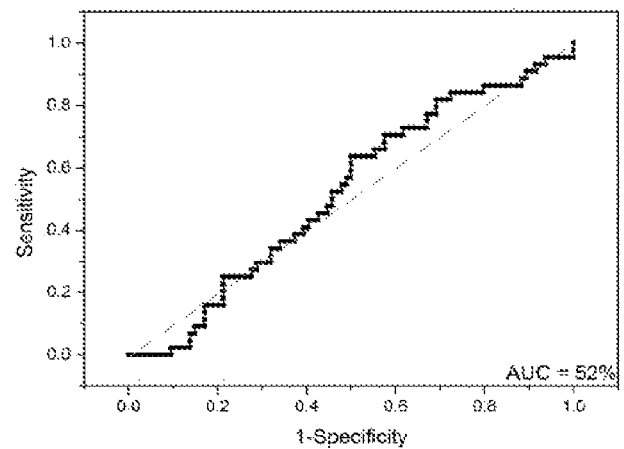
Figure 4C:
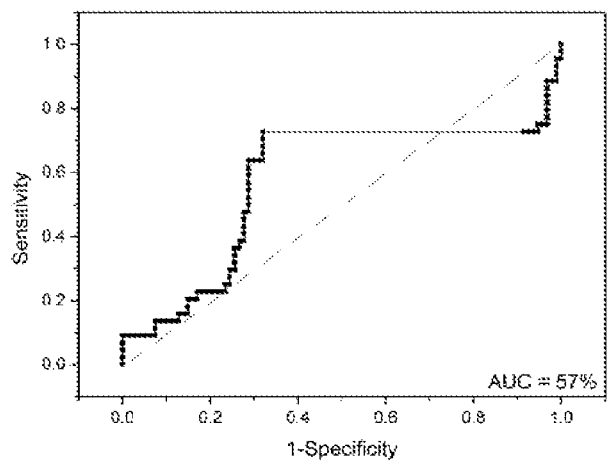
Figure 4D:
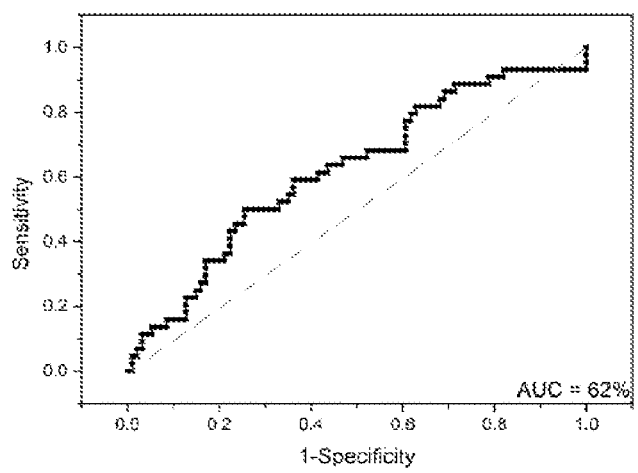
Figure 4E:
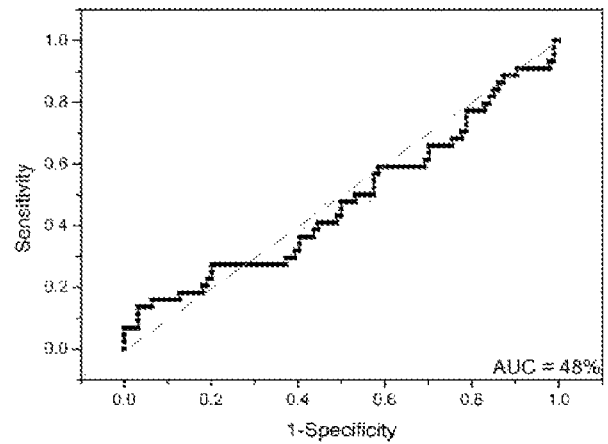

Sensors of functionalized single walled carbon nanotubes were formed by drop-casting a solution of SWCNTs (from ARRY International LTD, Germany; ~30% metallic, ~70% semiconducting, average diameter=1.5 nm, length=7 mm) in dimethylformamide (DMF, from Sigma Aldrich Ltd., >98% purity) onto the pre-prepared electrical transducers. The sensors were based on an electrically continuous random network of SWCNTs (U.S. Pat. Nos. 8,366,630; 8,481,324; the contents of each of which are hereby incorporated in their entirety). After the deposition, the device was slowly dried overnight under ambient conditions to enhance the self-assembly of the SWCNTs and to afford the evaporation of the solvent. The procedure was repeated until a resistance of 100 KΩ to 10 MΩ was obtained. The microelectronic transducer for the SWCNT sensor consisted of ten pairs of 4.5 mm wide, interdigitated Ti/Pd electrodes on silicon with two microns of thermal oxide (Silicon Quest International, Nevada, US). The gap between two adjacent electrodes was 100 μm. The SWCNT sensor was organically functionalized with 2-methyl-2-butene or with a Polycyclic Aromatic Hydrocarbon (PAH) derivative. The main structural properties of the PAH derivatives (PAH1-PAH6) used are presented in Table 2 and FIG. 3.

TABLE 2

Main structural properties of PAH derivatives

| PAH | Corona Core Shape | No. of Carbon Atoms in Corona | Side-Group Termination | Side-Group Type |
|---|---|---|---|---|
| PAH-1 | Hexagonal | 42 | Ether (methyl) | Weak polar |
| PAH-2 | Hexagonal | 42 | Ester (ethyl) | Strong polar |
| PAH-3 | Semi-Triangular | 48 | Ester (methyl) | Strong polar |
| PAH-4 | Semi-Triangular | 48 | Carboxyl | Strong polar |
| PAH-5 | Semi-Triangular | 48 | Carboxyl | Strong polar |
| PAH-6 | Hexagonal | 42 | Alcohol (hydroxyl) | Strong polar |

A total of twelve nanomaterial-based sensors were used to analyze the breath samples. Three sensors showed signal to noise ratios<3:1 and were thus excluded from the analysis. Accordingly, nine sensors were used for breath analysis with signal to noise ratios>3:1. A list of these sensors is provided Table 3.

TABLE 3

The nanomaterial-based sensors

| Base Material | Organic Functionality | Sensor's ID |
|---|---|---|
| Gold nanoparticles | dodecanethiol—morphology 1 | S02 |
|  | dodecanethiol—morphology 2 | S26 |
| Single-walled carbon nanotubes | 2-methyl-2-butene | S33 |
|  | PAH-1 | S10 |
|  | PAH-2 | S11 |
|  | PAH-3 | S12 |
|  | PAH-4 | S13 |
|  | PAH-5 | S14 |
|  | PAH-6 | S15 |

The GNP and SWCNT sensors used in this study responded rapidly and reversibly when exposed to typical VOCs in the breath with a very low responsivity to water vapors (Zilberman et al., Adv. Mater. 22, 4317-4320 (2010); Zilberman et al., Langmuir, 25, 5411-5416 (2009); Zilberman et al., ACS Nano, 5, 6743-6753 (2011); Peng et al., Nat. Nanotech., 4, 669-673 (2009); Peng et al., Nano Lett., 8, 3631-3635 (2008); and Konvalina et al., ACS Appl. Mater. Interfaces, dx.doi.org/10.1021/am2013695 (2011); the contents of each of which are hereby incorporated in their entirety). The latter is important due to the high background humidity in exhaled breath which may mask the signal of breath VOCs indicative of TB which are normally present in the breath at much lower concentrations. Moreover, in many diseases including TB, the composition of breath VOC biomarkers, which are generated by cellular biochemical processes, undergoes very subtle changes in VOCs' concentrations (Tisch et al., Rev. Chem. Eng., 26, 171-179 (2010); Amann et al., Euro. Resp. Soc. Monograph, 49, 96-114 (2010); and Amann et at, Mini-Rev. Med. Chem., 7, 115-129 (2007)).

It is noteworthy that in a typical batch production, about 70-76% of the produced sensors exhibit similar electrical and sensing behaviors with ±3% variance, which sensors are selected for clinical-related analysis. Reproducibility between different batches is estimated at ±3-4% variance. These variances are smaller than the responses obtained from the sensors. Additionally, the same sensors were used in all analyses (TB and control samples). Accordingly, these variances do not influence the obtained results. Typically, the fabrication costs of each sensor are estimated at ~80 cent/sensor with projected fabrication costs as low as ~15-20 cent/sensor using line production.

Statistical Analysis and Blind Experiment

The collective signals which were obtained from all sensors were analyzed using standard Principal Component Analysis (PCA; Roeck et al., Chem. Rev., 108, 705-725 (2008)). PCA is an effective method to reduce multidimensional data space to its main components and, therefore, improves the human perception of the data. The input variables used for PCA were the four features extracted from the sensors' responses. PCA provides the determination of the linear combinations of the sensor sensing features such that the maximum variance between all data points can be obtained in mutually orthogonal dimensions. The results represent the largest variance between sensor sensing features from the first principal component and produces decreasing magnitudes of variance from the second to the third principle components and so forth.

An independent set of 60 samples (20 TB positive, 20 TB negative and 20 healthy controls) were blindly picked from the 198 samples and were unlabeled and placed aside during the machine learning phase of data analysis. This set was used as a validation blind set. The remaining 138 samples (44 TB positive, 46 TB negative and 46 healthy controls) were used as a training set to search for odor specific sensitive sensors suitable for TB diagnosis. Receiver Operating Characteristic (ROC) curves were applied to the normalized responses of the 12 functional sensors, illustrating the performance of a binary classification (Patients vs. Controls) as the discrimination threshold varies. An arbitrary threshold of 80% accuracy was set to the sensors' classification of the 138 training set samples. Accordingly, only sensors which achieved a higher score than the threshold were used to classify the blind set. The sensitivity (True Positive/True positive+False negative), specificity (True Negative/True Negative+False Positive), accuracy (True Positive+True Negative/n), Positive Predictive Value (PPV=True positive/True positive+False Positive) and Negative Predictive Value (NPV=True Negative/True Negative+False Negative) of each test were calculated, evaluating the discriminative power of the diagnostic model. Statistical tests were performed by SAS JMP, Version 10.0.

Comparative Example

Three carbon nanotube-based sensors coated with PAH1-PAH3 and two gold nanoparticle-based sensors coated with tert-dodecanethiol or 2-ethylhexanethiol were tested to assess their ability to distinguish between TB positive and control samples. For each sensor, Youden's cut point (Best Sensitivity+Specificity-1) derived from ROC curve was used as classification cut-off. In all five sensors, the classification accuracy that was obtained was either random or slightly higher (accuracy range 54%-69%; Table 4). Furthermore, the area under the curves of 46%-57% range (FIGS. 4A-4E) also indicated that these sensors provide only poor discriminative ability between TB positive and control samples.

TABLE 4

Statistical analysis for the sensors

| Base Material | Organic Functionality | Accuracy | ROC Curve Area |
|---|---|---|---|
| Gold nanop articles | tert-dodecanethiol | 58% | 46% |
| Gold nanop articles | 2-ethylhexanethiol | 54% | 52% |
| Single-walled carbon nanotubes | PAH1 | 69% | 57% |

TABLE 4-continued

Statistical analysis for the sensors

| Base Material | Organic Functionality | Accuracy | ROC Curve Area |
|---|---|---|---|
| Single-walled carbon nanotubes | PAH2 | 65% | 62% |
| Single-walled carbon nanotubes | PAH3 | 69% | 48% |

Thus, these sensors are not suitable for the diagnosis of TB caused by *M. tuberculosis*.

Example 1: Identification of TB Patients Using a Single Nanomaterial-Based Sensor The feasibility of three sensors of the present invention to diagnose TB was tested by comparing breath samples of 44 TB positive patients to breath samples of 94 TB negative patients and healthy controls. Each sensor responded to all (or to a certain subset) of VOCs that were present in the exhaled breath samples. The sensing features were selected according to the accuracy of the training sets' differentiation between TB positive patients and control group (including both TB negative patients and healthy controls) using leave-one-out cross validation to determine the cut-off value between TB positive and healthy controls. The discriminative ability of all 12 normalized sensing features that were read from three sensors designated S02, S26 and S33 (four features per sensor) were compared. All the features discriminated well between the groups. The sensing features that were obtained from the dodecanethiol-coated gold nanoparticle sensors (S02 and S26) yielded slightly better results than the features from the SWCNT sensor. The discriminative ability of the sensing features was verified in a blind test, using 60 unknown test samples. Table 5 lists as an example, the classification test results for a training set that was used and a blind test using a single feature (i.e. F3) of sensor S26, which provided the best result. The blind test validation yielded values of over 90% for sensitivity, specificity and accuracy.

TABLE 5

Statistical classification success of TB, both on training set and blind test validation

|  | Single feature F3 of S26 | | Two-feature combinations | | | | PCA of all 12 sensing features | |
|---|---|---|---|---|---|---|---|---|
|  | | | F3 of S26 & F4 of S33 | | F2 of S02 & F2 of S33 | | F1-F4 of S02, S26 and S33 combined | |
| Sensing Features | Training Set | Blind Test | Training Set | Blind Test | Training Set | Blind Test | Training Set | Blind Test |
| True Positive | 37 | 18 | 40 | 18 | 39 | 18 | 40 | 18 |
| True Negative | 84 | 37 | 85 | 36 | 79 | 37 | 84 | 34 |
| False Positive | 10 | 3 | 9 | 4 | 15 | 3 | 10 | 6 |
| False negative | 7 | 2 | 4 | 2 | 5 | 2 | 4 | 2 |
| Accuracy (%) | 88 | 90 | 91 | 90 | 86 | 92 | 90 | 87 |
| Sensitivity (%) | 84 | 93 | 91 | 90 | 89 | 90 | 91 | 93 |
| Specificity (%) | 89 | 92 | 91 | 90 | 84 | 93 | 89 | 85 |

Figure 5A:
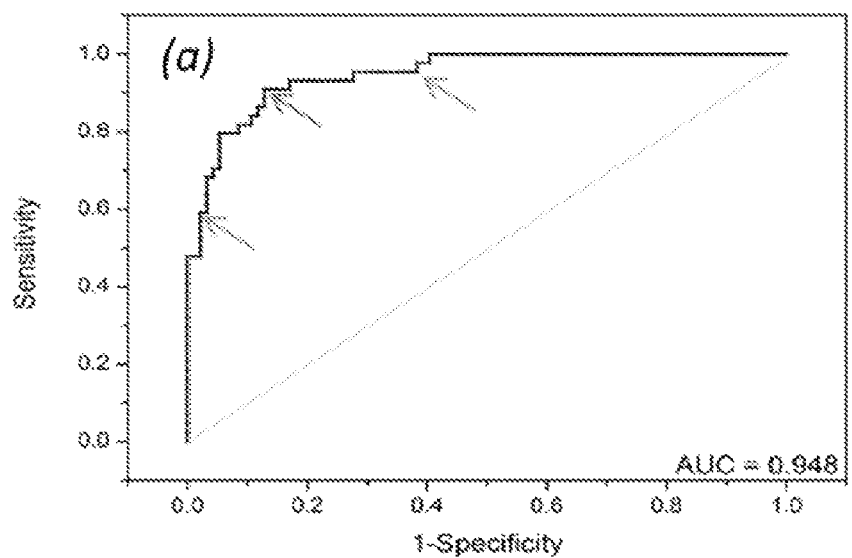
FIGS. 5A-5F. ROC curves (FIGS. 5A, 5C, 5E) and normalized sensing features (FIGS. 5B, 5D, 5F) of sensor 1 (S1.
Figure 5B:
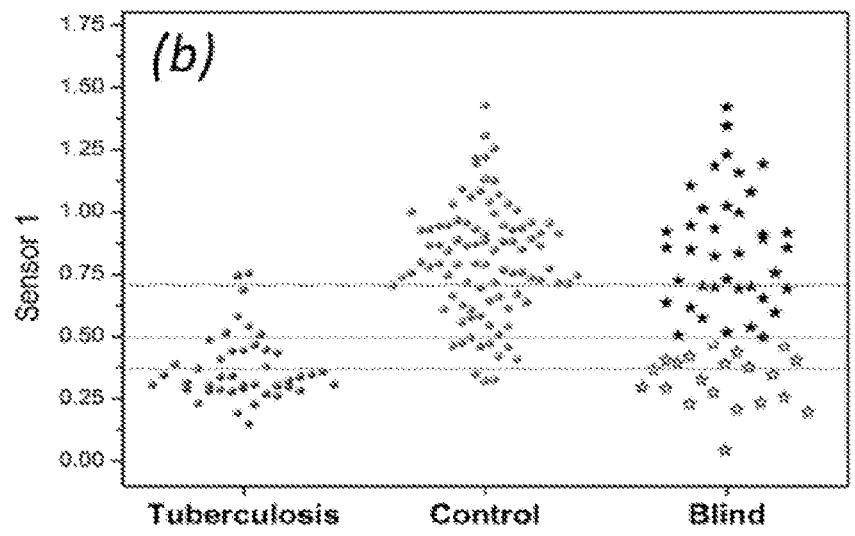

FIG. 5B shows the well separated clusters of TB positive and control populations that were obtained using a single feature (F3) of a single sensor of dodecanethiol-coated gold nanoparticles (S26). The cut-off value was set as 0.49. This was the cut-off value that was used for classifying the blind samples.

Figure 5C:
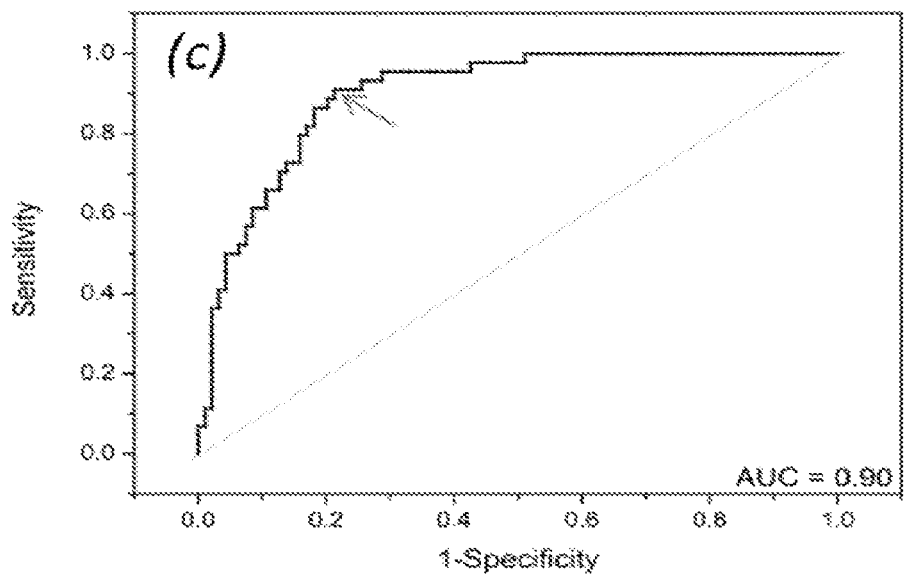
Figure 5D:
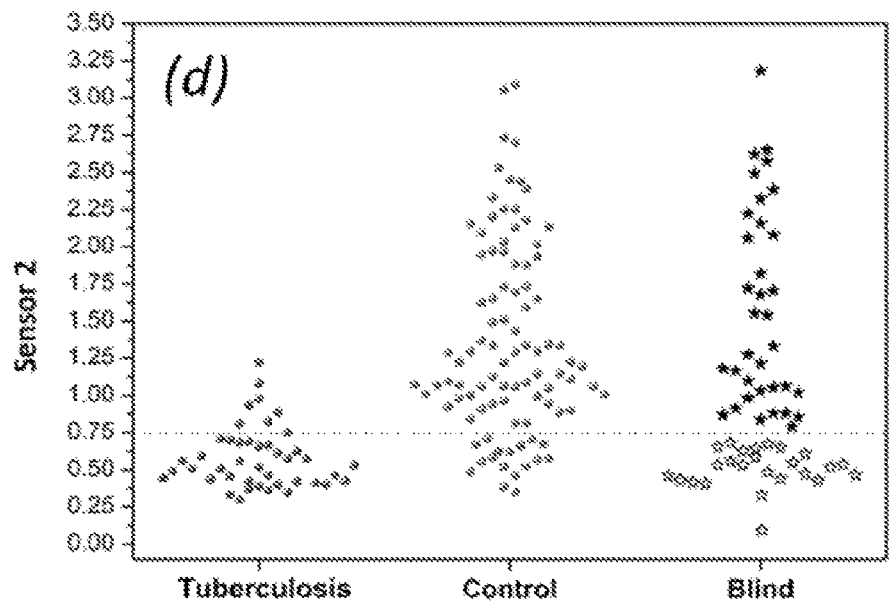
Figure 5E:
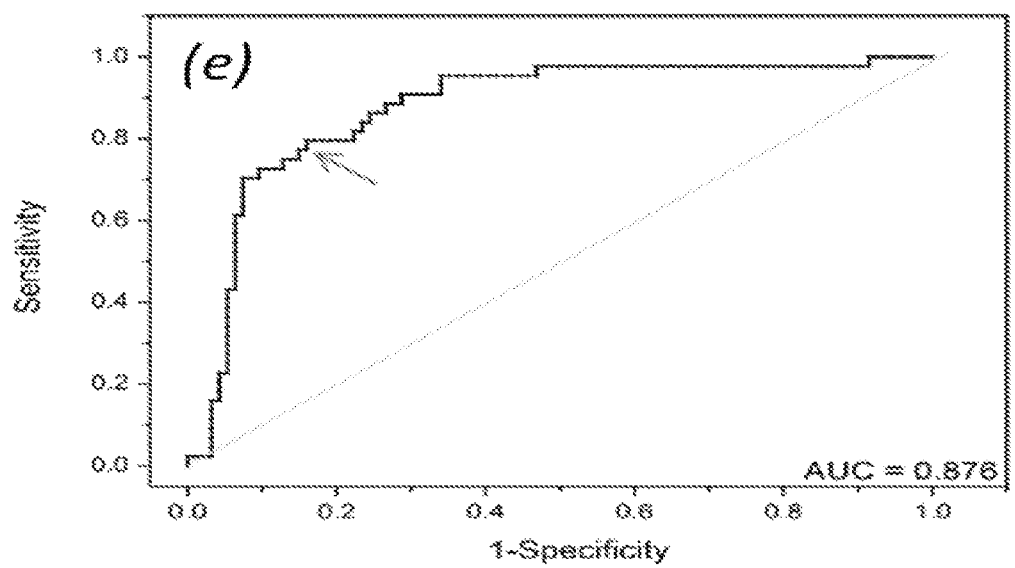
Figure 5F:
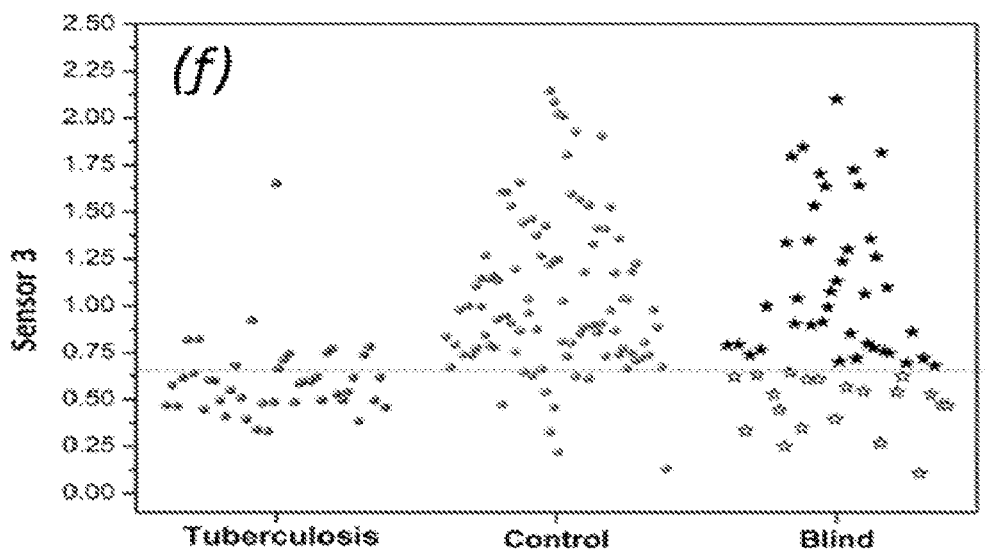

In particular, a threshold of 80% accuracy, in training set classification, when using Youden's cut point (Best Sensitivity+Specificity−1), was used for filtering out less sensitive sensors for TB detection. Three sensors were found to meet the standards, as the sensing features extracted from each of them presented powerful classification ability. These sensors were used for blind analysis of the breath samples. Two GNP-based sensors which were coated with dodecanethiol organic layer with slight surface morphology differences scored high results. The first sensor (GNP1) correctly classified 121 out of 138 training samples with an accuracy of 88%. The Area Under Curve (AUC) of ROC was 94.8%. When the same threshold was applied for validation set classification, the first sensor scored 90%, 93%, and 92% for sensitivity, specificity and accuracy, respectively. Moreover, when changing the threshold to higher sensitivity (95%), the NPV calculated by blind experiment was 94%. When lowering the rates of false negatives by increasing specificity of training set classification to 95%, a PPV of 93% was achieved (Table 6; FIGS. 5A-5B). The second sensor (GNP2) which was fabricated under very similar conditions was able to sharply distinguish between TB samples and control samples, with accuracy of 83% and 90% AUC of ROC. When classifying 60 unlabeled samples, with F2 sensing feature, 90% sensitivity, 82% specificity, with total accuracy of 85% was achieved (Table 6, FIGS. 5C-5D). The third sensor which comprises SWCNTs modified with 2-methyl-2-butene sensing layer (CNT1) scored a total accuracy of 86% in the blind experiment, with sensitivity of 80% and specificity of 90%. The results of the blind test were very close to the training set, where the accuracy was 84% and the AUC was 87.6% when ROC analysis was applied (Table 6, FIGS. 5E-5F). Hence, a single sensing feature and a single sensor of the present invention can be used to provide well separated clusters of TB positive and control populations and can therefore afford the differentiation of TB positive breath samples from controls. It is noteworthy that no significant difference between the sensors' response to healthy controls and TB negative samples were observed, even though the samples were collected at different locations due to safety regulations. Thus, the sensors of the present invention are essentially unaffected by the sampling surrounding, while being very sensitive to comprehensive alteration in exhaled breath composition, due to acute TB inflammatory process. A single sensor of the present invention provides the diagnosis of TB via breath analysis without the need for post-measurement analysis.

Example 2: The Responses of the Sensors to Main Confounding Factors

Figure 6A:
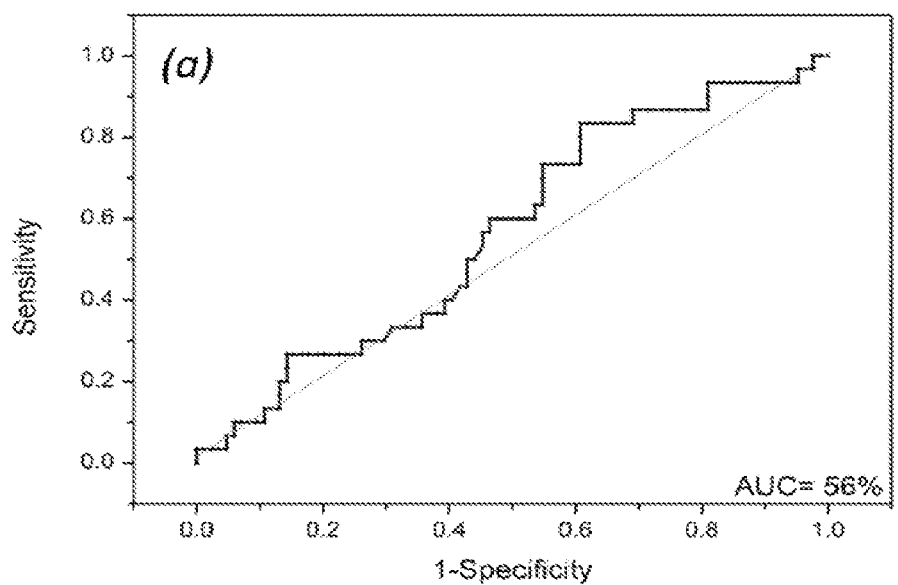
FIGS. 6A-6F. ROC curves (FIGS. 6A, 6C, 6E) and normalized sensing features (FIGS. 6B, 6D, 6F) of sensor 1 (S1), where (FIGS. 6A, 6B) refer to smoking habits of the study population, (FIGS. 6C, 6D) refer to HIV status among TB positive derivation set samples, and (FIGS. 6E, 6F) refer to medication status among the same group.
Figure 6B:
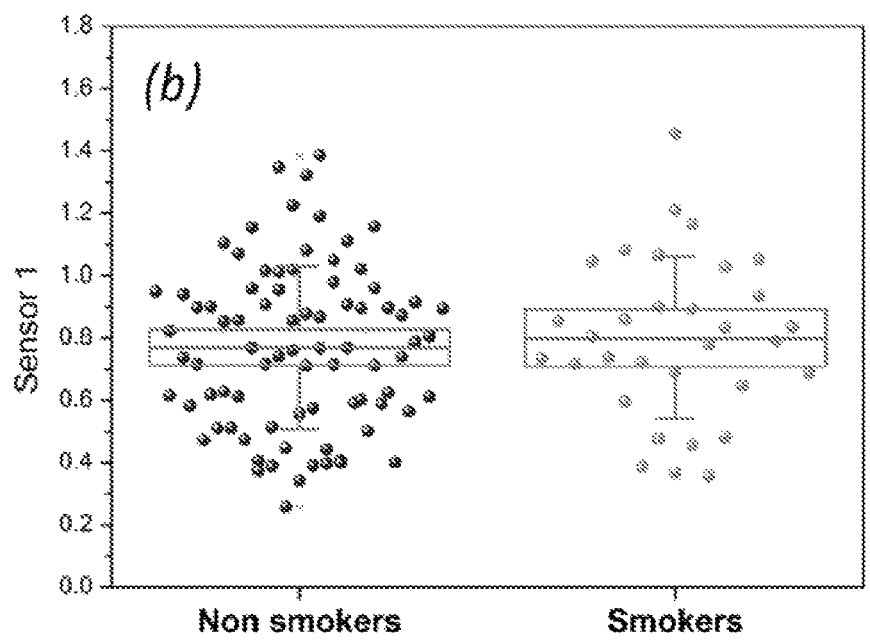
Figure 6C:
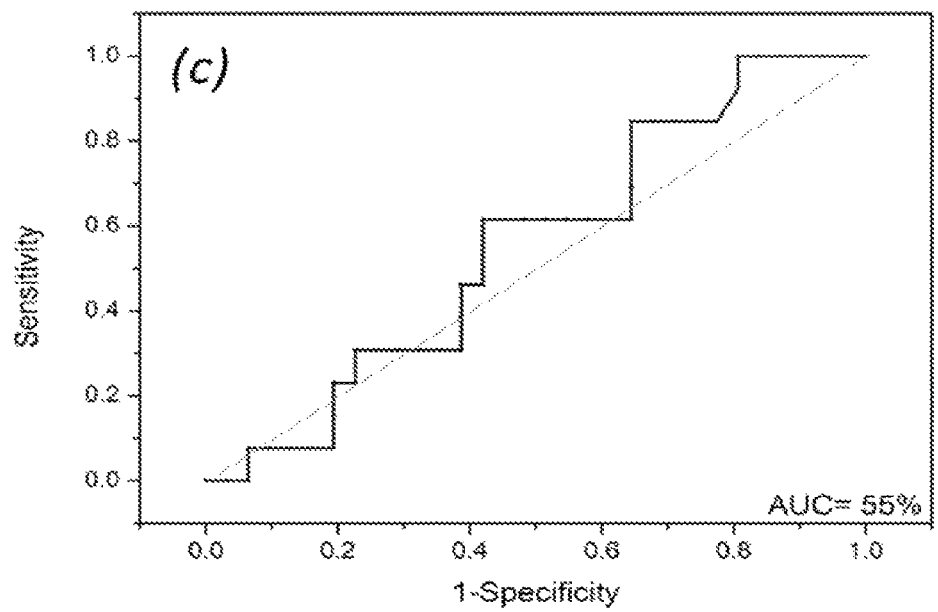
Figure 6D:
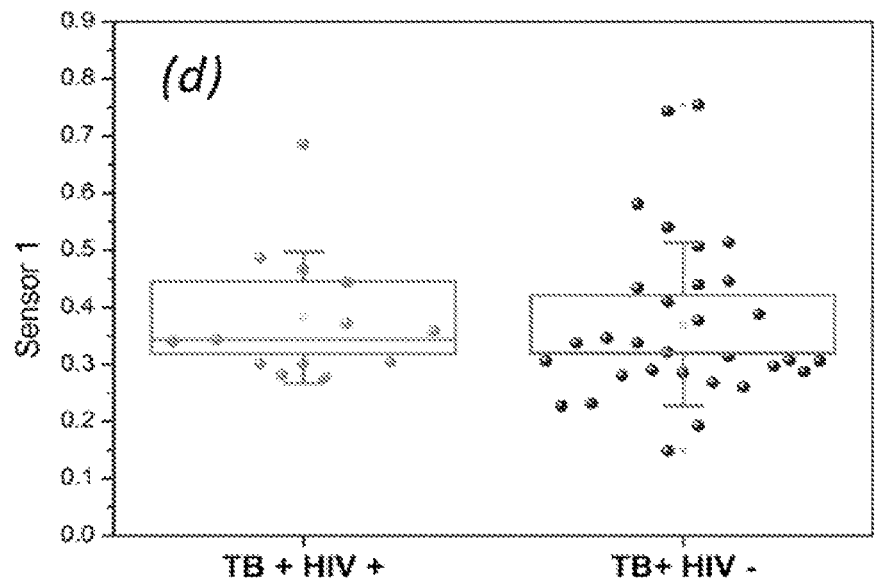
Figure 6E:
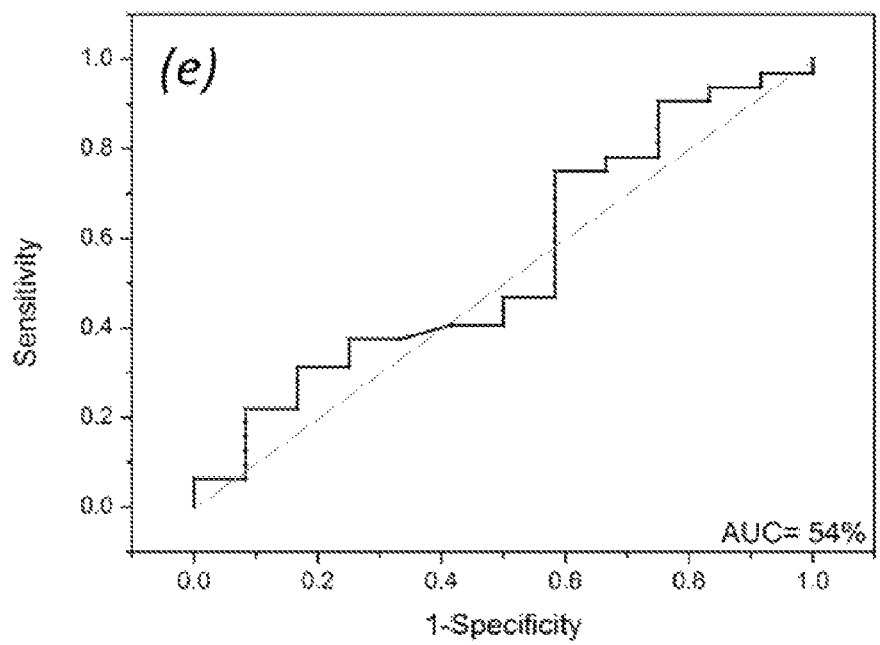
Figure 6F:
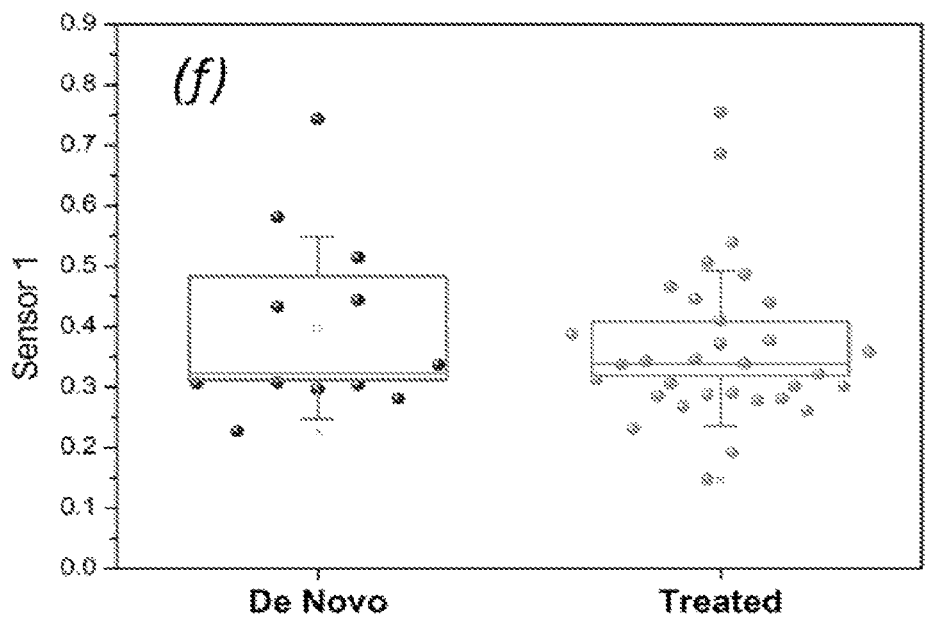

Tobacco smoking, TB medication and HIV co-infection of TB patients are important confounding factors that might affect the sensing signals. Accordingly, the effect of these three confounding factors on the sensors' readout signal was examined. It was found that none of the three sensors showed a significant response to the studied confounding factors. FIGS. 6A-6B show that the dodecanethiol coated GNP sensor of the present invention was not sensitive to tobacco smoking, even though smoking is known to cause significant changes to the chemical composition of human breath samples (Buszewski et al., Biomed. Chromatogr., 21, 553-566 (2007); Amann et al., Euro. Resp. Soc. Monograph, 49, 96-114 (2010); and Mickisch et al., Clinica Chimica Acta., 347 (1-2), 25-39 (2004)). The sensing signal of the same sensor to the breath samples of 44 TB positive patients did not distinguish between breath samples of HIV positive and HIV negative TB patients. The cluster of HIV positive TB patients completely overlaps with the cluster of HIV negative TB patients (FIG. 6D), showing that the sensor is not sensitive to HIV co-infection of the patients. Furthermore, newly diagnosed TB patients that did not receive any treatment (De Novo) could not be distinguished from TB patients that had received treatment (FIGS. 6E-6F). In all three cases, the results of leave-one-out cross validation were arbitrary. Thus, the sensor of the present invention correctly recognized 92% of the blind samples with no more than random detection ability regarding subjects' smoking habits, HIV status or medication treatment with ROC AUC of 56%, 55% and 54%, respectively. It is therefore concluded that the sensing signals of the sensors of the present invention are not affected by several important confounding factors, including smoking habits, TB medication and HIV co-infection.

TABLE 6

Statistical analysis results

| Sensor data | Cut point used | Training set Sensitivity/Specificity/Accuracy [%] | ROC AUC [%] | PPV [%] | NPV [%] | TP | FN | TN | FP | Blind set Sensitivity/Specificity/Accuracy [%] |
|---|---|---|---|---|---|---|---|---|---|---|
| GNP1 | Y§ | 85/89/88 | 94.8 | 78 | 92 | 18 | 2 | 37 | 3 | 90/93/92 |
| GNP1 | R-I* | 68/96/87 |  | 93 | 87 | 13 | 7 | 39 | 1 | 65/97/87 |
| GNP1 | R-O** | 95/83/86 |  | 78 | 96 | 19 | 2 | 34 | 6 | 95/85/88 |
| GNP2 | Y§ | 84/82/83 | 90 | 68 | 91 | 18 | 2 | 33 | 7 | 90/82/85 |
| CNT1 | Y§ | 75/89/84 | 87.6 | 76 | 87 | 16 | 4 | 36 | 4 | 80/90/86 |

§Youden's cut-point was derived from ROC curve, using the best (Sensitivity + Specificity − 1)
*Rule in cut-point chosen by 96% specificity in the training set classification
**Rule out cut-point chosen by 95% sensitivity in the training set classification
TP = True Positive;
FN = False Negative;
TN = True Negative;
FP = False Positive;
Sensitivity = (TP/TP + FN);
Specificity = (TN/TN + FP);
Accuracy = (TP + TN/n);
Positive Predictive Value (PPV) = (TP/TP + FP);
and Negative Predictive Value (NPV) = (TN/TN + FN)

Figure 7:
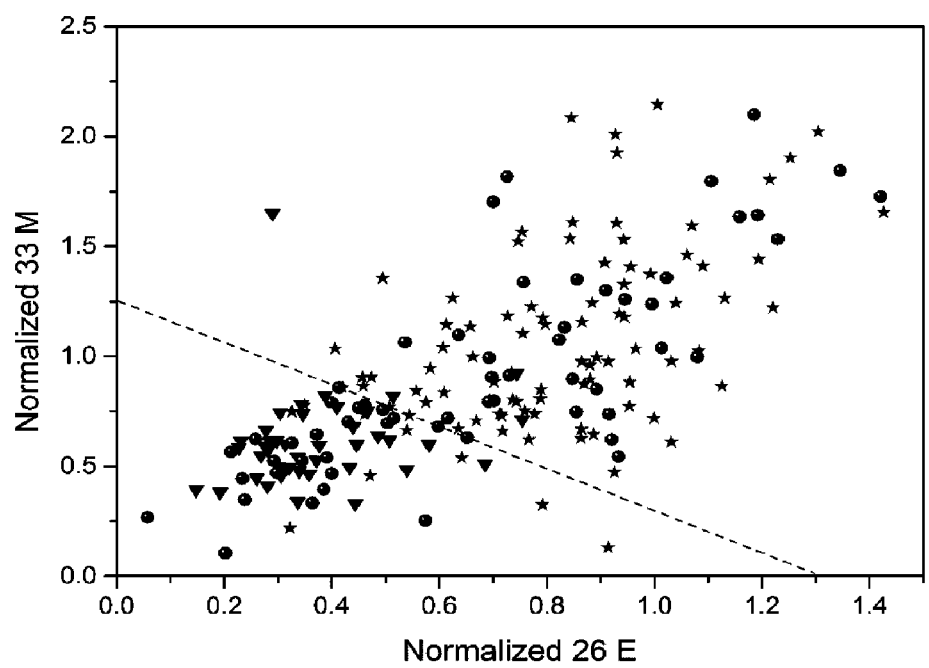
FIG. 7. Normalized resistance of a sensor of the present invention when exposed to breath samples. TB samples (▼), control samples (★), and blind samples (●). Blind samples below the cut-off (dashed line) were classified as TB positive.
Figure 8:
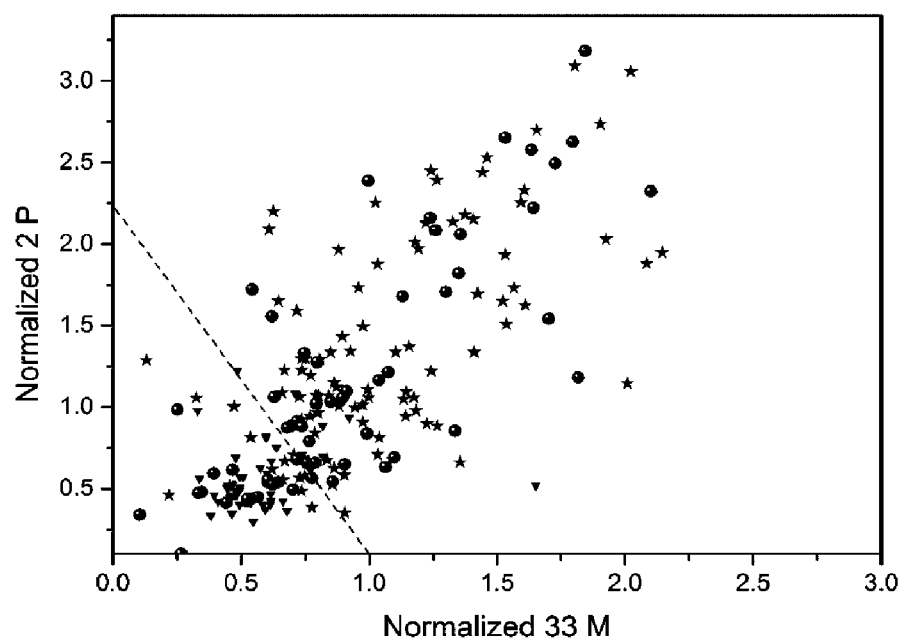
FIG. 8. Normalized resistance of two sensors (S33 and S02), when exposed to breath samples. TB samples (▼), control samples (★), and blind samples (●). Blind samples below the cut-off (dashed line) were classified as TB positive.
Figure 9:
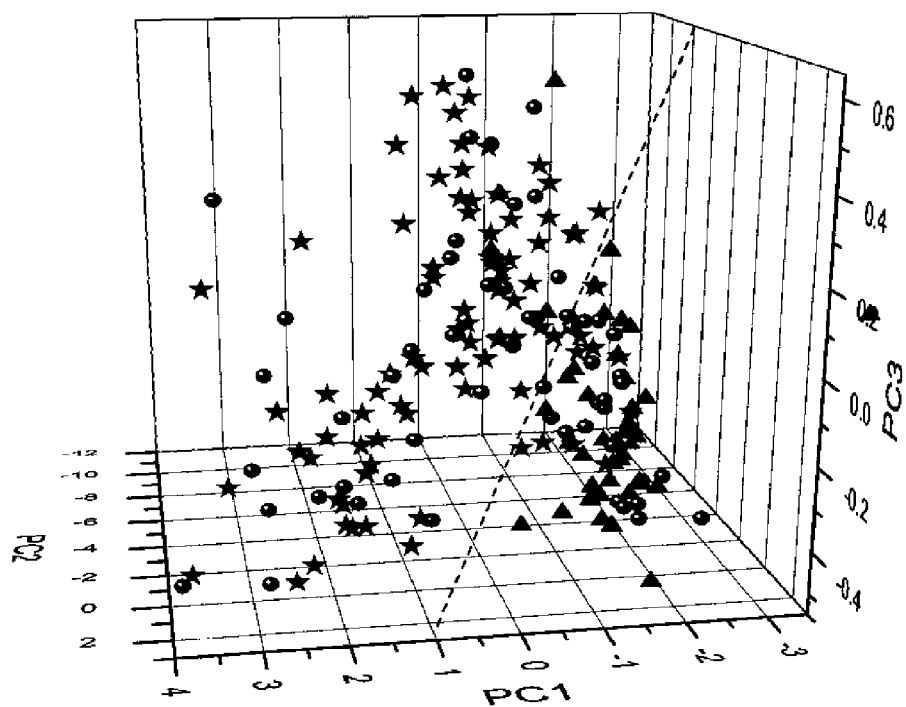
FIG. 9. Principal component analysis of the combined sensing signals from S02, S26 and S33, when exposed to breath samples. TB samples (▲), control samples (★), and blind samples (●). Blind samples below the cut-off (dashed line) were classified as TB positive.

Example 3: Identification of TB Patients Using a Sensor Array Comprising GNP- and SWCNT-Based Sensors The ability of an array of sensors of the present invention to identify TB patients was assessed using a combination of two different sensing features from three different sensors. In particular, one feature of the GNP-based sensors (S02, S26) and one feature of SWCNT-based sensor (S33) were used. The combination of two-features from three sensors yielded better classification results. The values for sensitivity, specificity and accuracy ranged from 80% to 93%. However, the maximal classification success did not exceed that of the best single sensing feature (F3 of sensor S26; see Table 5). FIGS. 7 and 8 show the two-dimensional plots of the combination of two different sensing features as representative examples. The dashed line represents the cut-off between the clusters of TB positive and control samples. The 2D clusters are well separated with little overlap between them. Table 5 lists the corresponding classification success. The values for the sensitivities, specificities and accuracies of the blind experiments were typically above 90%. Finally, the ability of an array of sensors of the present invention to identify TB patients was assessed using a combination of twelve sensing features from three different sensors. Principal component analysis of the combined signals showed that the cluster of TB samples is well separated from the cluster of control samples (FIG. 9). In particular, the clusters are well-separated by a dividing plane, whereby PC1, PC2 and PC3 cumulatively contain 93% of the data variance. Principle Component Analysis (PCA) yielded excellent classification success that was comparable to the typical classification success of the two sensor combinations (see Table 5).

Thus, the GNP and SWCNT sensors of the present invention are capable of identifying TB positive subjects and differentiate them from TB negative and healthy subjects in a blind experiment. Very high classification success with sensitivity, specificity and accuracy of more than 90% was achieved. The results were shown to be very reliable and reproducible. Increasing the number of readout signals did not improve the classification success. Hence, a single readout signal from a sensor of the present invention provides the diagnosis of TB caused by *M. tuberculosis* bacteria and can be used for breath testing of TB that could easily be adapted as a disposable home- or office-kit for fast TB testing, suitable for population screening.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A sensor for diagnosing tuberculosis caused by *M. tuberculosis* bacteria in a subject, the sensor comprising a nanomaterial selected from the group consisting of gold nanoparticles coated with dodecanethiol and single walled carbon nanotubes coated with 2-methyl-2-butene.

2. The sensor of claim 1 further comprising a substrate and a plurality of electrodes on said substrate.

3. The sensor of claim 2, wherein the gold nanoparticles coated with dodecanethiol or the single walled carbon nanotubes coated with 2-methyl-2-butene form a conductive path between the electrodes.

4. The sensor of claim 3, wherein upon adsorption of at least one volatile organic compound indicative of tuberculosis caused by *M. tuberculosis* bacteria on the dodecanethiol or 2-methyl-2-butene coating, the electrical conductivity between the electrodes changes thereby providing a measurable signal indicative of tuberculosis caused by *M. tuberculosis* bacteria.

5. The sensor of claim 1, configured in a form selected from the group consisting of a capacitive sensor, resistive sensor, a chemiresistive sensor, and an impedance sensor.

6. The sensor of claim 1, wherein the gold nanoparticles coated with dodecanethiol are in a configuration selected from 1D wires, 2D films, and 3D assemblies.

7. The sensor of claim 1, wherein the single walled carbon nanotubes coated with 2-methyl-2-butene are organized in a random network configuration.

8. The sensor of claim 1, wherein the nanomaterial is single walled carbon nanotubes coated with 2-methyl-2-butene.

9. The sensor of claim 1, wherein the nanomaterial is gold nanoparticles coated with dodecanethiol.

10. The sensor of claim 1, having tuberculosis detection sensitivity, specificity and accuracy of over 90%.

11. The sensor of claim 1, having a baseline resistance of about 2-10 MΩ.

* * * * *